United States Patent
Biffi et al.

(10) Patent No.: US 11,751,597 B2
(45) Date of Patent: Sep. 12, 2023

(54) COMPOSITIONS COMPRISING BACTERIAL STRAINS FOR USE IN INCREASING THE BIOAVAILABILITY OF AMINO ACIDS DERIVED FROM PROTEINS, AND RELATED FOOD PRODUCT METHODS AND SYSTEMS

(71) Applicant: ALFASIGMA S.P.A., Bologna (IT)

(72) Inventors: Andrea Biffi, Milan (IT); Walter Fiore, Milan (IT)

(73) Assignee: ALFASIGMA S.P.A., Bologna (IT)

( * ) Notice: Subject to any disclaimer, the term of this patent is extended or adjusted under 35 U.S.C. 154(b) by 0 days.

(21) Appl. No.: 17/090,669

(22) Filed: Nov. 5, 2020

(65) Prior Publication Data

US 2021/0186075 A1    Jun. 24, 2021

Related U.S. Application Data

(60) Provisional application No. 62/930,785, filed on Nov. 5, 2019.

(51) Int. Cl.
| C12N 1/20 | (2006.01) |
| A23L 33/135 | (2016.01) |
| A61K 35/747 | (2015.01) |

(52) U.S. Cl.
CPC .......... *A23L 33/135* (2016.08); *A61K 35/747* (2013.01)

(58) Field of Classification Search
None
See application file for complete search history.

(56) References Cited

U.S. PATENT DOCUMENTS

| 5,531,989 | A | 7/1996 | Paul |
| 6,770,246 | B1 | 8/2004 | Husek |
| 7,510,734 | B2 | 3/2009 | Sullivan et al. |
| 11,400,124 | B2 | 8/2022 | Biffi |
| 2002/0090416 | A1 | 7/2002 | Connolly |
| 2003/0031659 | A1 | 2/2003 | Farmer |
| 2003/0092163 | A1 | 5/2003 | Collins et al. |
| 2003/0157146 | A1 | 8/2003 | Rautonen et al. |
| 2003/0190369 | A1 | 10/2003 | Lovett |
| 2004/0170617 | A1 | 9/2004 | Finegold |
| 2005/0196480 | A1 | 9/2005 | Sullivan et al. |
| 2006/0057704 | A1 | 3/2006 | Schlothauer et al. |
| 2006/0067921 | A1 | 3/2006 | Conway |
| 2008/0081035 | A1 | 4/2008 | Parmely et al. |
| 2008/0193603 | A1 | 8/2008 | Hayes et al. |
| 2008/0241226 | A1 | 10/2008 | Abeln et al. |
| 2009/0061446 | A1 | 3/2009 | Niimi et al. |
| 2009/0098088 | A1 | 4/2009 | Taylor et al. |
| 2009/0220481 | A1 | 9/2009 | Maes et al. |
| 2009/0274662 | A1 | 11/2009 | Magowan et al. |
| 2009/0312282 | A1 | 12/2009 | Yoshida et al. |
| 2010/0074994 | A1 | 3/2010 | Harel et al. |
| 2010/0112564 | A1 | 5/2010 | Zhao et al. |
| 2011/0014167 | A1 | 1/2011 | Bindels et al. |
| 2011/0038837 | A1 | 2/2011 | Nishida et al. |
| 2011/0052538 | A1* | 3/2011 | Brown ............ A61P 3/08 424/93.42 |
| 2011/0166100 | A1 | 7/2011 | Wu |
| 2011/0305744 | A1 | 12/2011 | Russo |
| 2012/0251512 | A1 | 10/2012 | Farmer et al. |
| 2012/0269865 | A1 | 10/2012 | Roughead et al. |
| 2012/0301451 | A1 | 11/2012 | Braenning et al. |
| 2012/0322773 | A1 | 12/2012 | Pravda |
| 2016/0296569 | A1 | 10/2016 | Guglielmetti et al. |
| 2016/0348155 | A1 | 12/2016 | Guglielmetti et al. |
| 2017/0035816 | A1 | 2/2017 | Biffi |
| 2019/0192590 | A1 | 6/2019 | Biffi |
| 2019/0290706 | A1 | 9/2019 | Biffi et al. |
| 2019/0345268 | A1 | 11/2019 | Biffi et al. |
| 2021/0236565 | A1 | 8/2021 | Biffi |

FOREIGN PATENT DOCUMENTS

| CN | 1161795 A | 10/1997 |
| CN | 1701116 A | 11/2005 |
| CN | 1840206 A | 10/2006 |
| CN | 101636173 A | 1/2010 |
| CN | 102919922 A | 2/2013 |
| CN | 108743851 A | 11/2018 |
| EP | 1145643 A1 | 10/2001 |
| EP | 2407532 A2 | 1/2012 |

(Continued)

OTHER PUBLICATIONS

Balzaretti et al (Frontiers in Microbio. Sep. 2015. vol 6. Article 952, pp. 1-13).*
Tuohy et al (J.Applied Microbio. 2007. 102: 1026-1032).*
Balzaretti S. et al., "A novel hetero-exopolysaccharide mediates the recognition of Lactobacillus paracasei DG by the immune system" Pharmabiotics Conference2015, Paris, Oct. 29-30, 2015, 1 page.
Bienenstock J et al., "New insights into probiotic mechanisms" *Gut Microbes*, vol. 4 Issue 2, Apr. 2013, 7 pages.
Canadian Examination Search Report for CA Application No. 2,923,390 filed on Sep. 5, 2014 on behalf of SOFAR S.P.A. dated Jan. 26, 2021 4 pages.
Communication pursuant to Article 94(3) EPC for EP Application No. 14790322.3 filed on Sep. 5, 2014 on behalf of SOFAR S.P.A. dated Jan. 11, 2021 3 pages.

(Continued)

*Primary Examiner* — Jennifer E Graser
(74) *Attorney, Agent, or Firm* — Steinfl + Bruno LLP

(57) ABSTRACT

Compositions, food products, methods and systems for use in increasing the blood bioavailability of amino acids derived from proteins, preferably proteins of plant origin, comprising a mixture M comprising or, alternatively, consisting of at least one bacterial strain, preferably *Lactobacillus paracasei* DG® CNCM I-1572 and/or *Lactobacillus paracasei* LPC-S01™ DSM 26760, and possibly. The compositions food products, methods and systems o the disclosure, can further comprise at least one protein, preferably proteins of plant origin, or a peptide or an amino acid, and in particular includes a food product comprising proteins, preferably of plant origin, and said mixture M of at least one bacterial strain.

13 Claims, 1 Drawing Sheet

(56) References Cited

FOREIGN PATENT DOCUMENTS

| | | |
|---|---|---|
| JP | H0517363 A | 1/1993 |
| JP | 2005508617 A | 4/2005 |
| JP | 2005534315 A | 11/2005 |
| JP | 2010512755 A | 4/2010 |
| JP | 2010161944 A | 7/2010 |
| JP | 2013515051 A | 5/2013 |
| RU | 2182008 C1 | 5/2002 |
| WO | 00/54788 A1 | 9/2000 |
| WO | 2003/090763 A1 | 11/2003 |
| WO | 2004/022727 A1 | 3/2004 |
| WO | 2005/001109 A2 | 1/2005 |
| WO | 2005/083122 A2 | 9/2005 |
| WO | 2006/050479 A2 | 5/2006 |
| WO | 2007/071815 A1 | 6/2007 |
| WO | 2007/140621 A1 | 12/2007 |
| WO | 2008/119012 A2 | 10/2008 |
| WO | 2008/148798 A2 | 12/2008 |
| WO | 2010/008272 A1 | 1/2010 |
| WO | 2010/008278 A1 | 1/2010 |
| WO | 2010/099824 A1 | 9/2010 |
| WO | 2011/036539 A1 | 3/2011 |
| WO | 2012/154738 A1 | 11/2012 |
| WO | 2014/068338 A1 | 5/2014 |
| WO | 2014/137211 A1 | 9/2014 |
| WO | 2015/000972 A1 | 1/2015 |
| WO | 2015/033304 A1 | 3/2015 |
| WO | 2015/033305 A1 | 3/2015 |
| WO | 2015/162570 A1 | 10/2015 |
| WO | 2015/172191 A1 | 11/2015 |
| WO | 2016/030320 A1 | 3/2016 |
| WO | 2017/195182 A1 | 11/2017 |
| WO | WO 2017/195182 * | 11/2017 |
| WO | 2017/212433 A1 | 12/2017 |
| WO | 2018/100549 A1 | 6/2018 |
| WO | 2018/109520 A1 | 6/2018 |
| WO | 2018/109730 A1 | 6/2018 |
| WO | 2019/019961 A1 | 1/2019 |
| WO | 2019/053604 A1 | 3/2019 |
| WO | 2019/111189 A1 | 6/2019 |
| WO | 2021/053636 A1 | 3/2021 |
| WO | 2021/053639 A1 | 3/2021 |
| WO | 2021/053641 A2 | 3/2021 |
| WO | 2021/053642 A1 | 3/2021 |
| WO | 2021/090228 A1 | 5/2021 |
| WO | 2021/090228 A4 | 7/2021 |

OTHER PUBLICATIONS

Declaration for the self-archiving of the doctoral thesis for "Exploring Lactobacillius Paracasei Probiosis and Metabolic Potential" by Balzaretti, Silvia Dated: Nov. 20, 2015 5 pages (English + Original).

Laws A. et al., "Determination of the structure and molecular weights of the exopolysaccharide produced by Lactobacillus acidophilus 5e2 when grown on different carbon feeds." Carbohydr Res.Feb. 4, 2008;343(2):301-7.

Notice of Allowance for U.S. Appl. No. 16/301,361, filed Nov. 13, 2018 on behalf of SOFAR S.P.A. dated Feb. 1, 2021 8 pages.

Paoluzi O.A., et al. "Low efficacy of levofloxacin-doxycycline-based third-line tripletherapy for Helicobacter pylori eradication in Italy." World Journal of Gastroenterology21: 6698-705,Jun. 2015.

Rosania R. et al. "Effect of probiotic or prebiotic supplementation on antibiotic therapy in the small intestinal bacterial overgrowth: a comparative evaluation." Gurr Clin Pharmacol. May 2013;8(2):169-72. 5 pages.

Aden K. et al., "Metabolic Functions of Gut Microbes Associate with Efficacy of Tumor Necrosis Factor Antagonists in Patients with Inflammatory Bowel Diseases" Gastroenterology, 2019, pp. 1279-1292.

Allegretti J. et al., "Short Chain Fatty Acid Profiles Are Altered by Fecal Microbiota Transplantation for the Treatment of Inflammatory Bowel Disease and Recurrent Clostridioides difficile Infection" Gastroenterology,2019, 2 pages.

Australian Examination Report for AU Application No. 2017263294 filed on May 15, 2017 on behalf of SOFAR S.P.A. dated Oct. 30, 2020 5 pages.

Ausubel et al, Current Protocols in molecular biology, edited vols. 1 and 2. John Wiley & Sons, Inc., Media, PA, 1994.

Balzaretti et al., "A Novel rhamnose-rich heterp-exopolysaccharide isolated from Lactobacillus paracasei DG activates THP-1 human monocytic cells" University of Huddersfiled Repository Article for Applied and Environmental Microbiology.Jan. 17, 2017.

Balzaretti et al., "Exploring Lactobacillus paracasei probiosis and metabolic potential", University of Milan PhD thesis, 2015, pp. 1-132.

Balzaretti S. et al., "The vaginal isolate Lactobacillus paracasei LPC-S01 (DSM 26760) is suitable for oral administration" Frontiers in Microbiology, vol. 6, art. 952,Sep. 2015 , 13 pages.

Banasiewicz T. et al., "Determination of butyric acid dosage based on clinical and experimental studies—a literature review" Gastroenterology Review,2020, pp. 119-125.

Borren N. et al., "Alterations in Fecal Microbiomes and Serum Metabolomes of Fatigues Patients With Quiescent Inflammatory Bowel Diseases" Clinical Gastroenterology and Hepatology,Mar. 2020, 35 pages.

Canadian Office Action for CA Application No. 2,923,392 filed on Sep. 5, 2014 on behalf of SOFAR S.P.A. dated Jun. 1, 2020 4 pages.

Cassard L. et al, "Individual strains of Lactobacillus paracasei differentially inhibit human basophil and mouse mast cell activation," Immunity, Inflammation, and Disease vol. 4, Issue 3., 2016. 11 Pages.

Chassard C. et al., "Functional dysbiosis within the gut microbiota of patients with constipated-irritable bowel syndrome" Alimentary Pharmacology and Therapeutics,2012, pp. 828-838.

Chilean Office Action for CL Application No. 201803193 filed on Sep. 5, 2014 dated Apr. 16, 2020 16 pages (English + Original).

Chinese Decision of Rejection for CN Application No. 201480049296.4 filed on Sep. 5, 2014 on behalf of SOFAR S.P.A. dated Dec. 9, 2020 (English + Original) 12 pages.

Chinese Office Action for CN Application No. 201480049288 filed on Sep. 5, 2014 on behalf of SOFAR S.P.A. dated Sep. 16, 2020 8 pages (English + Original).

Ciucanu I. et al. "A simple and rapid method for the permethylation of carbohydrates" Carbohydrate Research,131 (1984) pp. 209-217.

Collins M.N. and Birkinshaw C. "Hyaluronic acid based scaffolds for tissue engineering—A review", Carbohydrate Polymers 2013, 1262-1279.

Colombian Office Action for CO Application No. NC2018/0010950 filed on Sep. 5, 2014 on behalf of SOFAR S.P.A. dated Jul. 27, 2020 11 pages (Partial English + Original).

Communication pursuant to Article 94(3) EPC for EP Application No. 14790322.3 filed on Sep. 5, 2014 on behalf of SOFAR S.P.A. dated Jan. 31, 2020 8 pages.

Compare D. et al., "Lactobacillus easel DG and its postbiotic reduce the inflammatory mucosal response: an ex-vivo organ culture model of post-infectious irritable bowel syndrome" BMC Gastroenterology,2017, 8 pages.

Costalos et al., "Enteral feeding of premature infants with Saccharomyces boulardii" Early Human Development, 74,(2003), 89-96.

Cremon C. et al., "Effect of Lactobacillus paracasei CNCM I-1572 on symptoms, gut microbiota, short chain fatty acids, and immune activation in patients with irritable bowel syndrome: A pilot randomized clinical trial" UEG Journal,Sep. 2017, 10 pages.

Crohn's and Colitis Foundation of America. Inflammatory Bowel Disease and Inflammatory Bowel Syndrome: Similarities and Differences. 2014. 12 Pages.

Cui Y. et al., "Revolution of Chronic Diarrhoea" China Medicine, Science, and Technology Publishing House, 1st edition, Jan. 2013, pp. 19-23 (Original + Partial Google Translation).

De Souza M.M. et aJ. "Effects of budesonide and probiotics enemas on the systemic inflammatory response of rats with experimental coJitis", Acta Cirurgica Brasileira 2007, 22 (Supp 1. 1 ): 40-45.

Di Mario Francesco et al., "Use of mesalazine in diverticular disease." Journal of Clinical Gastroenterology. vol. 40, Suppl 3, Aug. 2006.

(56) References Cited

OTHER PUBLICATIONS

D'Inca R. et al. Rectal administration of Lactobacillus Casei DG modifies flora composition and Toll-Like receptor expression in colonic mucosa of patients with mildulcerative colitis'\ Dig. Dis. Sci. 2011, 56: 1178-1187.

EFSA Journal, "Scientific Opinion on the maintenance of the list of QPS biological agents intentionally added to food and feed (2012 update)1" EFSA Journal 2012; 10(12):3020. 84 pages.

Eurasian Notification of Grant for Application No. 201690464/28 filed on Sep. 5, 2014 on behalf of SOFAR S.P.A. dated Jun. 9, 2020 2 pages (English + Original).

European Food Safety Authority EFSA journal (2012) 10(6): 2723.

Evans S. "Clinical trial structures" *J Exp Stroke Transl Med*.Mar. 2011, pp. 1-16, 16 pages.

"Example Cross-Over Study Design {A Phase 11, Randomized, Double-Blind Crossover Study of Hypertena and Placebo in Participants with High Blookd Pressure)". ClinicalTrials.gov (2012).

Fakhari A. and Berkland C. "Applications and emerging trends of hyaluronic acid in tissue engineering, as a dermal fIller and in osteoarthritis treatment", Acta Biomaterialia 2013, 9, 7081-7092.

Fao and Who et al; "Live microorganisms which, when administered in adequate amounts, confer a health benefit on the host", *World Health Organizations and Food Agriculture Organization*. 2001.

Farup et al., "Probiotics, Symptoms, and Gut Microbiota; What are the relations? A Randomized Controlled Trial in Subjects with Irritable Bowel Syndrome" Gastro Research and Practice, vol. 2012. 7 pages.

Ferrario et al J. Nutrition (published online Sep. 3, 2014) 144: 1787-1796 (Year: 2014).

Final Office Action for U.S. Appl. No. 14/916,959, filed Mar. 4, 2016 on behalf of SOFAR S.P.A. dated Aug. 21, 2020 48 pages.

Final Office Action for U.S. Appl. No. 14/916,959, filed Mar. 4, 2016 on behalf of SOFAR SPA. dated Jul. 23, 2019. 23 pages.

Final Office Action for U.S. Appl. No. 14/916,961, filed Mar. 4, 2016 on behalf of SOFAR S.P.A dated Jan. 2, 2020 16 pages.

Final Office Action for U.S. Appl. No. 15/305,470, filed Oct. 20, 2016 on behalf of SOFAR S.P.A. dated Jul. 10, 2020 21 pages.

Final Office Action for U.S. Appl. No. 16/301,361, filed Nov. 13, 2018 on behalf of SOFAR S.P.A. dated Sep. 21, 2020 11 pages.

Final Office Action for U.S. Appl. No. 14/916,961, filed Mar. 4, 2016 on behalf of SOFAR S.P.A. dated Mar. 13, 2018. 15 pages.

Final Office Action for U.S. Appl. No. 15/305,470, filed Oct. 20, 2016 on behalf of SOFAR SPA. dated Jan. 14, 2019. 10 pages.

Final Office Action for U.S. Appl. No. 14/916,959, filed Mar. 4, 2016 on behalf of SOFAR SPA. dated Apr. 20, 2018. 26 pages.

Fiorino et al., "P325Efficacy and Safety of IBD98E, a Sodium Hyaluronate Topical Preparation, in theInduction of Clinical and Endoscopic Remission in Patients with DistalUlcerative Colitis: An Open Label Pilot Study," *United European GastroenterologyJournal*:1 (1S) (A219).Oct. 2013.

Floch M.H. et al. "Recommendations for probiotic use—2011 Update", J. Clin.Gastroenterol. 2011, 45: S168-S171.

Food and Agriculture Organization. Health and nutritional properties of probiotics in food including powder milk with live lactic acid bacteria. Oct. 2001: 34 pages.

Gargari G. et al., "Fecal Clostridiales distribution and short-chain fatty acids reflect bowel habits in irritable bowel syndrome" Environmental Microbiology, Sep. 2018, 31 pages.

Gerwig G. et al., "Determination of the absolute configuration of mono-saccharides in complex carbohydrates by capillary G.L.C." *Carbohydrate Research*,77(1979) pp. 1-7.

Gill et al., "Metagenomic Analysis of the Human Distal Gut Microbiome," Science 312: 1355-1359 (2006).

Guglielmetti S. et al., "TgaA, a VirB1 -Like Component Belonging to a Putative Type IV Secretion System of Bifidobacterium bifidum MIMBb75" *Applied and Environmental Microbiology*,vol. 80, No. 17,Sep. 2014 pp. 5161-5169.

Gugliemetti et al., "Randomised clinical trial; Bifidobacterium bifidum MIMBb75 significatnly alleviates irritable bowel syndrome and improves quality of life, a double-blind, placebo-controlled study" Alimentary Pharmacology & Therapeutics, p. 1123-1132. 2011.

Guo, Y., et al., "Irritable Bowel Syndrome is Positively Related to Metabolic Syndrome: A Population-Based Cross-Sectional Study," PLoS One. 9(11): e112289. Nov. 10, 2014. 6 pages.

Havea P. "Protein interactions in milk protein concentrate powders" *International Dairy Journal*,vol. 16,2006, pp. 415-422.

Hustoft T. et al., "Effects of varying dietary content of fermentable short-chain carbohydrates on symptoms, fecal microenvironment, and cytokine profiles in patients with irritable bowel syndrome" Neurogastroenterology & Motility, Sep. 2016, 9 pages.

International Search Report for International Application No. PCT/IB2014/064284 filed on Sep. 5, 2014 on behalf of SOFAR SPA. dated Jan. 26, 2015. 6 pages.

International Search Report for International Application No. PCT/IB2014/064285 filed on Sep. 5, 2014 on behalf of SOFAR SPA. dated Jan. 29, 2015. 4 pages.

International Search Report for International Application No. PCT/IB2017/052850 filed on May 15, 2017 on behalf of SOFAR SPA. dated Aug. 17, 2017. 4 pages.

International Search Report for International Application No. PCT/IB2017/053389 filed on Jun. 8, 2017 on behalf of SOFAR SPA. dated Oct. 6, 2017. 5 pages.

International Search Report for International Application No. PCT/IB2017/057576 filed on Dec. 1, 2017 on behalf of SOFAR SPA. dated Feb. 22, 2018. 5 pages.

International Search Report for International Application No. PCT/IB2017/057980 filed on Dec. 15, 2017 on behalf of SOFAR SPA. dated Mar. 19, 2018. 4 pages.

International Search report for International Application PCT/IB2015/052938 filed on Apr. 22, 2015 on behalf of SOFAR SPA. dated Jul. 31, 2015. 4 pages.

Irritable Bowel Syndrome—Wikipedia, dated Sep. 16, 2020. 33 pages, https://en.wikipedia.org/wiki/Irritable_bowel_syndrome.

Israeli Office Action for Application No. 244391 filed on Mar. 2, 2016 on behalf of SOFAR S.P.A. dated Jun. 24, 2020 4 pages (English + Original).

Israeli Office Action for Application No. 269107 filed on Sep. 3, 2019 on behalf of SOFAR S.P.A. dated May 17, 2020 5 pages (English + Original).

Israeli Office Action for IL Application No. 244391 filed on behalf of SOFAR S.P.A. dated Oct. 27, 2020 (English + Original) 4 pages.

Italia il Ministero della Salute (*Linee Guida su Probiotici e Prebiotici rev*.May 2013).

Jacobsen et al., "Screening of Probiotic Activities of Forty-Seven Strains of Lactobacillus spp. By In Vitro techniques and Evaluation of the Colonization Ability of Five Selected Strains in Humans" Applied and Environmental Microbiology, Nov. 1999, p. 4949-4956. 8 pages.

Japanese Office Action for JP Application No. 2016564193 filed on Apr. 22, 2015 on behalf of SOFAR S.P.A. dated Feb. 18, 2020 11 pages (English + Original).

Kay, RM., et al., "Dietary Fiber," J. of Lipid Research, v. 23, 1982. 221-242, 22 Pages.

Langhorst J. et al., "Distinct patterns of short-chain fatty acids during flare in patients with ulcerative colitis under treatment with mesalamine or a herbal combination of myrrh, chamomile flowers, and coffee charcoal: secondary analysis of a randomized controlled trial" European Journal of Gastroenterology & Hepatology, Feb. 2020, 6 pages.

Larsen et al., "Predominant genera of fecal microbiota in children with atopic dermatitis are not altered by intake of probiolic bacteria Lactobacillus acidophilus NCFM and Bifidobacterium animalis subsp. lacis Bi-07," FEMS Microbiol Ecol 75: 482-496 (2011).

Laws et al., "Biosynthesis, characterization, and design of bacterial exopolysacharides from lactic acid bacteria", *Biotechnology Advances*. vol. 19,2001. pp. 597-625.

LeBlanc et al., "Beneficial effects on host energy metabolism of shot-chain fatty acids and vitamins produced by commensal and probiotic bacteria," Microbial Cell Factories 16:79: 1-10 (2017).

(56) References Cited

OTHER PUBLICATIONS

Intermountain Healthcare. 2015. Irritable Bowel Syndrome (IBS). Retrieved from: https://intermountainhealthcare.org/services/gastroenterology/conditions/irritable-bowel-syndrome/. 2015. 3 pages.
Lombardo L; et al "New insights into Lactobacillus and functional intestinal disorders", Minerva Gastroenterologica E Dietologica, Edizioni Minerva Medica, Torino, IT, vol. 54, No. 3. 2008.
Lombardo, Lucio et al., "Clinical Evaluation of Lactobacillus Paracasei Subsp. Paracasei F19 with Gluco-Oligosaccharides in the Short-term Treatment of Irritable Bowel Syndrome" Microbial Ecology in Health and Disease 21: 28-32 (2009).
Magnusson M. et al., "The Anti-inflammatory Immune Regulation Induced by Butyrate is Impaired in Inflamed Intestinal Mucosa from Patients with Ulcerative Colitis" Inflammation, Apr. 2020, 11 pages.
Martin R. et al. "Role of commensal and probiotic bacteria in human health: a focus on inflammatory bowel disease", Microbial Cell Factories 2013, 12: 71.
Matthes H. et al. "Clinical trial: probiotic treatment of acute distal ulcerative colitis with rectally administered *Escherichia coli* Nissle I 917 (EcN)", BMC Complementaty and Alternative Medicine 2010, 10:13.
Mazzuoli S. et al. "Definition and evaluation of mucosal healing in clinical practice", Digestive and Liver Disease 2013, 45, 969-977.
Mcfarland, et al., "Strain-Specificity and Disease—Specificity of Probiotic Efficacy: A Systematic Review and Meta-Analysis," Frontiers in Medicine, May 7, 2018. 14 Pages.
Mexican Office Action for MX Application No. MX/a/2016/002766 filed on Sep. 5, 2014 on behalf of SOFAR S.P.A. dated Aug. 13, 2020 10 pages (English + Original).
Michail et al., "Gut Microbiota is Not Modified by Randmized, Double-Blind, Placebo-Controlled Trial of VSL #3 in Diarrhea-Predominant Irritable Bowel Syndrome". (Probiotics & Antimicro Prot. (2011) 3: 1-7).
Milani et al., Assessing the fecal microbiota: and optimized ion torrent 16S rRNA gene-based analysis protocol. PLoS One. 2013; 8(7); e68739, 12 pages. Published 2013.
Montalto M. et al., "Clinical trial: the effects of a probiotic mixture on non-steroidal anti-inflammatory drug enteropathy—a randomized, double-blind, cross-over, placebo-controlled study" *Aliment Pharmacol Ther*,2010, pp. 209-214, 6 pages.
Muyzer et al., "Profiling of Complex Microbial Populations by Denaturing Gradient Gel Electrophoresis Analysis of Polymerase Chain Reaction-Amplified Genes Coding for 16S rRNA," Applied and Environmental Microbiology 59: 595-700(1993).
Necas J. et al. "Hyaluronic acid (hyaluronan): a review", Veterinarni Medicina, 2008, 53(8): 397-411.
Neiwert et al., "Structural Investigation of rhamnose-rich polysaccharides from *Streptococcus dysgalactiae* bovine mastitis isolate" Carbohydrate Research, vol. 389, 2014. pp. 192-195.
Non-Final Office Action for U.S. Appl. No. 16/308,330, filed Dec. 7, 2018 on behalf of SOFAR S.P.A.. dated May 14, 2020. 23 Pages.
Non-Final Office Action for U.S. Appl. No. 14/916,961, filed Mar. 4, 2016 on behalf of SOFAR S.P.A. dated Jun. 30, 2017. 21 pages.
Non-Final Office Action for U.S. Appl. No. 14/916,961, filed Mar. 4, 2016 on behalf of SOFAR S.P.A. dated Jul. 25, 2019. 18 pages.
Non-Final Office Action for U.S. Appl. No. 15/305,470, filed Oct. 20, 2016 on behalf of SOFAR SPA. dated Aug. 22, 2019. 8 pages.
Non-Final Office Action for U.S. Appl. No. 16/301,361, filed Nov. 13, 2018 on behalf of SOFAR S.P.A. dated May 8, 2020 20 pages.
Non-Final Office Action for U.S. Appl. No. 14/916,961, filed Mar. 4, 2016, on behalf of SOFAR S.P.A. dated Jan. 7, 2021. 22 Pages.
Non-Final Office Action for U.S. Appl. No. 14/916,959, filed Mar. 4, 2016 on behalf of SOFAR S.P.A. dated Mar. 13, 2020 25 pages.
Non-Final Office Action for U.S. Appl. No. 14/916,959, filed Mar. 4, 2016 on behalf of SOFAR SPA. dated Aug. 31, 2017. 27 pages.
Non-Final Office Action for U.S. Appl. No. 14/916,959, filed Mar. 4, 2016 on behalf of SOFAR SPA. dated Nov. 19, 2018. 15 pages.
Non-Final Office Action for U.S. Appl. No. 15/305,470, filed Oct. 20, 2016 on behalf of SOFAR SPA. dated Mar. 26, 2018. 10 pages.

Office Action in corresponding Chinese Patent Application No. 201480049296.4, dated Aug. 27, 2019.
Office Action in Corresponding Japanese Patent Application No. 2016-564193, dated Apr. 2, 2019.
Okuda et al., "Virtual metagenome reconstruction from 16S rRNA gene sequences". *Nature Communications*,2012. 8 pages.
Oliva S. et al. "Randomised clinical trial: the effectiveness of Lactobacillus Reuteri ATCC 55730 rectal enema in children with active distal ulcerative colitis", Aliment. Pharmacol. Ther. 2012, 35: 327-334.
Olveira et al; "Lactobacillus paracasei Reduces Intestinal Inflammation in Adoptive Transfer Mouse Model of Experimental Colitis", Clinical and Developmenta Immunology, vol. 23, No. 5, Jan. 1, 2011, pp. 1077-13.
Orlando A. et al. "Clinical implications of mucosal healing in the management of patients with inflammatory bowel disease", Digestive and Liver Disease 2013, 45, 986-991.
Pituch A. et al., "Butyric acid in functional constipation" *Przeglad Gastroenterologiczny*,2013, 4 pages.
Plant et al., "Association of Laclobacillus spp. with Peyer's Patches in Mice", Clinical and Diagnostic Laboratory Immunology 8: 320-324 (2001).
Polak-Berecka et al., "Physiocochemical characterization of exopolysaccharides produced by lactobacillus rhamnosus on various carbon sources", Carbohydrate Polymers, vol. 117, 2015. pp. 501-509.
Pozuelo M. et al., "Reduction of butyrate and methane producing microorganisms in patients with Irritable Bowel Syndrome" *Nature Scientific Reports*,Apr. 2015, 12 pages.
Price R.D. et al. "Hyaluronic acid: the scientific and clinical evidence", Journal of Plastic, Reconstructive & Aesthetic Surgery2007, 60: 1110-1119.
Ralf Jager et al., "Probiotic Administration Increases Amino Acid Absorption from Plant Protein: a Placebo-Controlled, Randomized, Double-Blind, Multicenter, Crossover Study," Probiotics and Antimicrobial Proteins, 2020. 10 Pages.
Restriction Requirement for U.S. Appl. No. 16/465,237, filed May 30, 2019 on behalf of SOFAR S.P.A. dated Dec. 21, 2020 8 pages.
Restriction Requirement for U.S. Appl. No. 14/916,961, filed Mar. 4, 2016 on behalf of SOFAR S.P.A. dated May 10, 2019. 7 pages.
Ringel-Kulka T. et al., "Short Chain Fatty Acids and Intestinal Transit in Patients With Irritable Bowel Syndrome and Healthy Controls" *AGA Abstracts*,May 2012, 1 page.
Sambrook et al. Molecular cloning: A Laboratory Manual. 3rd ed., vols. 1,2 and 3 cold Spring Harbor Laboratory Press, 2001, 2100 pp.
Sanlibaba et al., "Exopolysaccharides production by lactic acid bacteria", *Applied Microbiology*, vol. 2,May 20, 2016.
Sasaki M. et al., "Transglucosidase improves the gut microbiota profile of type 2 diabetes mellitus patients: a randomized double-blind, placebo-controlled study" *BMC Gastroenterology*, 13:81,2013.
Savino et al., "Laclobacillus reuteri DSM 17938 in Infantile Colic: A Randomized, Double-Blind, Placebo-Controlled Trial", Pediatrics 126: e526-e533 (2010).
Scaldaferri F. et al. "Gut microbial flora, prebiotics and probiotics in IBD: their current usage and utility", BioMed Research International 2013, 9 pages.
Scarpellini E. et al., "Efficacy of butyrate in the treatment of diarrhea-predominant irritable bowel syndrome" Digestive and Liver Disease, 2007, 4 pages.
Shi Y. et al., "Function and clinical implications of short-chain fatty acids in patients with mixed refractory constipation" Association of Coloproctology of Great Britain and Ireland, Feb. 2016, 8 pages.
Siew Chien Ng et al., "Effect of probiotic bacteria on the intenstinal microbiota in irritable bowel syndrome" Journal of gastroenterology and hepatology. 2013.
Smokvina T. et al "Lactobacillus paracasei Comparative Genomics: Towards Species Pan-Genome Definition and Exploitation of Diversity," Plos One, Jul. 19, 2013. 16 Pages.
Spiller et al., "Randomized double blind placebo-controlled trial of *Saccharomyces cerevisiae* CNCM I-3856 in irritable bowel syndrome: improvement in abdominal pain and bloating in those with predominant constipation" *United European Gastroenterology Journal*. 2016.

(56) References Cited

OTHER PUBLICATIONS

Stuknyte M. et al., "Potential immunomodulatory activity of bovine casein hydrolysates produced after digestion with proteinases of lactic acid bacteria" *International Dairy Journal*, 21(2011) pp. 763-769.

Sun Q. et al., "Alterations in fecal short-chain fatty acids in patients with irritable bowel syndrome" *Systematic Reviewand Meta-Analysis*,Jan. 2019, 12 pages.

Taverniti and Gugliemetti et al., "The immunomodulatory properties of probiotic microorganisms beyond their viability (ghost probiotics: proposal of paraprobiotic concept)" Department of Food Science and Microbiolgy (DiSTAM), , 6:261-274 (2011).

Third Chinese Office Action for CN Application No. 201480049296.4 filed on Sep. 5, 2014 on behalf of SOFAR S.P.A. dated Mar. 18, 2020 13 pages (English + Original).

Turco F. et al., Bacterial stimuli activate nitric oxide colonic mucosal production in diverticular disease. Protective effects of L. casei DG (Lactobacillus paracasei CNCM I-1572) UEG Journal, Nov. 2016, 10 pages.

Turco F. et al., "Enteroglial-derived S100B protein integrates bacteria-induced Toll-like receptor signalling in human enteric glial cells" GUT Neurogastroenterology, vol. 63, Mar. 2014, Originally Published online Jan. 3, 2013, 12 pages.

Turnbaugh et al., "The Effect of Diel on the Human Gut Microbiome: A Metagenomic Analysis in Humanized gnolobiotic Mice," Sci Transl Med: (2009).

Tursi A. et al., "Assessment of Fecal Microbiota and Fecal Metabolome in Symptomatic Uncomplicated Diverticular Disease of the Colon" *J. Clin Gastroenterol*,Oct. 2016, 4 pages.

Tursi A. et al., "Fecal Microbiota, Fecal and Urinary Metabolic Profiling and Symptomatic Uncomplicated Diverticular Disease of the Colon" *Digestive and Liver Disease*, 2017, 1 page.

Tursi A. et al., "Natural History of Symptomatic Uncomplicated Diverticular Disease: A 13-Year Prospective Study" *AGA Abstracts*,Apr. 2017, 1 page.

Tursi et al., "Balsalazide and/or high-potency probiotic mixture (VSL#3) in maintaining remission after attack of acute, uncomplicated diverticulitis of the colon", International Journal of Colorectal Disease; Clinical and Molecular Gastroenterology an Surgery, Sprinter, Berlin, DE. vol. 22, No. 9, Mar. 28, 2007. pp. 1103-1108.

Tursi et al., "Effect of Lactobacillus easel supplementation on the effectiveness and tolerability of a new second-line 10-day quadruple therapy after failure of a first attempt to cure Helicobacter pylori infection," Med Sci Monit 10: CR662-666 (2004).

Tursi et al., "Mesalazine and/or Lactobacillus Casei in maintaining Long-term Remission of Symptomatic Uncomplicated Diverticular Disease of the Colon" Original Paper. Hepato-Gastroenterology. 2008, 55; 916-920.

Tursi et al., "Mesalazine and/or Lactobacillus casei in preventing recurrence of symptomatic uncomplicated diverticular disease of the colon: A Prospective , randomized, open-label study", Journal of Clinical Gastroenterol, Raven Press LTD, NY, New York. vol. 40, No. 2, Apr. 1, 2006. pp. 312-316.

Tursi et al., "Randomised clinical trial: mesalazine and/or probiotics in maintaining remission of symptomatic uncomplicated diverticula disease—double-blind, randomized, placebo-controlled study" Alimentary Pharmacology & Therapeutics. vol. 38, No. 7. Oct. 19, 2013. pp. 741-751.

U.S. National Library of Medicine, "Effect of Lactobacillus Casei DG (Enterolactis Plus) in Patient with irritable Bowel Syndrome: a Pilot Study", ClinicalTriaals.gov, Feb. 11, 2015.

U.S. National Library of Medicine Efficacy Evaluation of a Commercial Preparation Containing Lactobacillus Casei DG on the Reduction of the Painful Symptoms Related to the Irritable Bowel Syndrome (IBS). *A Pilot Clinical Study*.28, Feb. 2014.

Valerio et al., "Effects of Probiotic Lactobacillus paracasei-enriched Artichokes on Constipated Patients", J Clin Gastroenterol, Sep. 10, 2010.

Vernia et al. Dig. Disease Sci. (1988) 33(11): 1353-135 (Year: 1988).

Vinogradov et al., "Structural studies of the rhamnoseirch cell wall polysaccharide of lactobacillus casei BL23" *Carbohydrate Research* vol. 435,Oct. 8, 2016. pp. 156-161.

Wang Y. et al., "Emerging Infectious Diseases" Science and Technology Documents Publishing House, 1 st edition, Jan. 2006, pp. 310-312 (Original + Partial Google Translation).

Watanabe I. et al., "KT-11" *Food Style* 21, vol. 17, No. 6, pp. 62-64,2013. 5 pages (Machine Translation + Original).

"Why VSL#3" (Obtained from https://vsl3.com/hcp/vsl-info on Aug. 22, 2017, 4 pages.

Worthley et al. "A human, double-blind, placebo-controlled, cross-over trial of prebiotic, probiotic, and symbiotic supplementation: effects on luminal, inflammatory, epigenetic, and epithelial biomarkers of colorectal cancer" (Am J Clin Nutr 2009; 90; 578-86).

Written Opinion for International Application No. PCT/IB2014/064284 filed on Sep. 5, 2014 on behalf of SOFAR SPA. dated Jan. 26, 2015. 7 pages.

Written Opinion for International Application No. PCT/IB2014/064285 filed on Sep. 5, 2014 on behalf of SOFAR SPA. dated Jan. 29, 2015. 7 pages.

Written Opinion for International Application No. PCT/IB2017/052850 filed on May 15, 2017 on behalf of SOFAR SPA. dated Aug. 17, 2017. 6 pages.

Written Opinion for International Application No. PCT/IB2017/053389 filed on Jun. 8, 2017 on behalf of SOFAR SPA. dated Oct. 6, 2017. 7 pages.

Written Opinion for International Application No. PCT/IB2017/057576 filed on Dec. 1, 2017 on behalf of SOFAR SPA. dated Feb. 22, 2018. 8 pages.

Written Opinion for International Application No. PCT/IB2017/057980 filed on Dec. 15, 2017 on behalf of SOFAR SPA. dated Mar. 19, 2018. 8 pages.

Written Opinion for International Application PCT/IB2015/052938 filed on Apr. 22, 2015 on behalf of SOFAR SPA. dated Jul. 31, 2015. 5 pages.

Zhang et al., "Isolated exopolysaccharides from lactobacillus rhamnosus GG alleviated adipogenesis mediated by TLR2 in mice" *Scientific reports*. vol. 6,Oct. 27, 2016.

Zheng, L. et al. "Regulation of colonic epithelial repair in mice by toll-like receptors and hyaluronic acid," Gastroenterology 2009: 137 2041-2051.

Zhuang M. et al., "Abundance of probiotics and butyrate-production microbiome manages constipation via short-chain fatty acids production and hormones secretion" Molecular Nutrition & Food Research, Jul. 2019, 41 pages.

Zhuang M. et al., "Systematic Review and Meta-analysis: Short-Chain Fatty Acid Characterization in Patients With Inflammatory Bowel Disease" *Inflammatory Bowel Disease*,Nov. 2019, 13 pages.

Colombian Office Action for CO Application No. NC2018/0010954 filed on Nov. 1, 2018 on behalf of SOFAR S.P.A. dated Feb. 5, 2021 9 pages (Partial English + Original).

Colombian Office Action for CO Application No. NC2019/0007116 filed on Jul. 2, 2019 on behalf of SOFAR S.P.A. dated Jan. 15, 2021 19 pages (English + Original).

Mexican Office Action for MX Application No. MX/a/2016/002766 filed on Sep. 5, 2014 on behalf of SOFAR S.P.A. dated Mar. 18, 2021 10 pages (English + Original).

Screenshot from the web-archive of the Milano University, Nov. 23, 2015, 2 pages (English + Original).

Allowance of the Brazilian patent application BR 11 2016 005059 2 published in the Official Bulletin no 2651 of Oct. 26, 2021 (Portuguese Only).

Australian Examination Report for AU Application No. 2017367302 filed on Dec. 1, 2017 on behalf of SOFAR S.P.A. dated Jul. 23, 2021 4 pages.

Bacteriotherapy—Merriam-Webster Medical Dictionary, Archive Date: Apr. 26, 2016, 6 pages.

Bassi R. "Mesalazine + Lactobacillus paracasei CNCMI1572 vs Mesalazine alone in preventing recurrence of symptom of diverticular disease: a prospective, randomize, open-label study." *Colorectal Disease*, 2019 1 pages.

(56) References Cited

OTHER PUBLICATIONS

Bassi R. "Preventing recurrence of symptomatic diverticular disease of the colon: mesalazine with or without Lactobacillus case DG: a prospective randomized, open label study." European Society of Coloproctology, 2015, 1 page.
Canadian Office Action for CA Application No. 2,923,392 filed on Sep. 5, 2014 on behalf of SOFAR S.P.A. dated Apr. 1, 2021 4 pages.
Canani R. B. et al., "Potential beneficial effects of butyrate in intestinal and extraintestinal diseases" World Journal of Gastroenterology, vol. 17 No. 12, Mar. 2011, 10 pages.
Capsule (Pharmacy)—Wikipedia, the free encyclopedia, Archive Date: Apr. 10, 2016, 4 pages.
Chilean Office Action for CL Application No. 201901493 filed on Dec. 1, 2017 on behalf of SOFAR S.P.A. dated May 6, 2021 24 pages (English + Original).
Chinese Office Action for CN Application No. 201480049288X filed on Sep. 5, 2014 on behalf of SOFAR S.P.A. dated Aug. 12, 2021 (English + Original) 15 pages.
Chooi E. et al., "Chronic atrophic gastritis is a progressive disease: analysis of medical reports from Shanghai (1985-2009)" Singapore Med J, 2012, 53 (5), pp. 318-324.
Colledge H. "Atrophic Gastritis: Causes. Symptoms, & Treatment" *Healthline*, Sep. 2018, 5 pages.
Colombian Office Action for CO Application No. NC2018/0010950 filed on May 15, 2017 on behalf of SOFAR S.P.A. dated May 3, 2021 9 pages (English + Original).
Colombian Office Action for CO Application No. NC2018/0010954 filed on Jun. 2, 2019 on behalf of SOFAR S.P.A. dated Jun. 30, 2021 8 pages (Partial English + Original).
Colombian Office Action for CO Application No. NC2019/0007116 filed on Jul. 2, 2019 on behalf of SOFAR S.P.A. dated Sep. 29, 2021 12 pages (English + Original).
Colombian Office Action for Colombian Application No. NC2019/0006257 filed on Dec. 15, 2017 on behalf of SOFAR S.P.A. dated May 13, 2021 3 pages (English + Original).
Communication pursuant to Article 94(3) EPC for EP Application No. 17817173.2 filed on Dec. 1, 2017 on behalf of SOFAR S.P.A. dated Sep. 29, 2021 6 pages.
De Backer A. I. et al., "Intestinal stenosis from mesenteric injury after blunt abdominal trauma" Eur. Radiol., 1999, pp. 1429-1431.
Dore J. et al., "The Human Intestinal Microbiota; From Phylogenetics to Functional Metagenomics" *Old Herborn University*, 2010, pp. 15-26.
Dysbiosis—Wikipedia, the free encyclopedia, Dated: Mar. 31, 2014 https://web.archive.org/web/20140331225522/http://en.wikipedia.org/wiki/Dysbiosis , 4 pages.
Eurasian Office Action for EA Application No. 202090097/28 filed on Sep. 5, 2014 on behalf of SOFAR S.P.A. dated Aug. 16, 2021 (English + Original) 10 pages.
Ferrario, et al., "Modulation of Fecal Clostridiales Bacteria and Butyrate by Probiotic Intervention with Lactobacillus paracasei DG Varies among Healthy Adults1-3" J. Nutritional Epidemiology, 144. Sep. 3, 2014. pp. 1787-1796. 10 Pages.
Final Office Action for U.S. Appl. No. 14/916,959, filed Mar. 4, 2016 on behalf of SOFAR S.P.A. dated Dec. 29, 2021. 29 Pages.
Final Office Action for U.S. Appl. No. 14/916,961, filed Mar. 4, 2016, on behalf of SOFAR S.P.A. dated Oct. 14, 2021. 26 Pages.
Gould M. et al., "Diabetic diarrhea" Current Gastroenterology Report, 2009, pp. 354-359 (Abstract only).
Gould, M., et al., "Diabetic Diarrhea," Current Gastroenterology Reports, 11: 354-359. Full paper. 2009. 7 Pages.
Haenel H. "Human Normal and Abnormal Gastrointestinal Flora" *American Journal of Clinical Nutrition*, vol. 23 No. 11, Nov. 1970, pp. 1433-1439.
Iebba V. et al., "Eubiosis and Dysbiosis: the two sides of the microbiota" *New Microbiologica*, vol. 39, 2016, pp. 1-12.
Jarbrink-Sehgal M. E. et al., "Symptomatic Diverticulosis is Characterized by Loose Stools" *Clinical Gastroenterology and Hepatology*, 14: 1763-1770, Dec. 2016, 9 pages.

John Hopkins Medicine—Fecal Transplantation (Bacteriotherapy), John Hopkins Division of Gastroenterology and Hepatology, Archive Date: Apr. 2016, 2 pages.
Laval G. et al., "The use of steroids in the management of inoperable intestinal obstruction in terminal cancer patients: do they remove the obstruction?" Palliative Medicine, 2000, pp. 3-10.
Leonel, A.J., et al. "Butyrate: implications for intestinal function," Current Opinion in Clinical Nutrition and Metabolic Care 15(5): 474-479. 2012. 6 Pages.
Mangili G. et al., "Palliative care for intestinal obstruction in recurrent ovarian cancer: a multivariate analysis" *BMJ Journals*, 2005, 5 pages (Abstract Only).
Miceli E. et al., "Common Features of Patients with Autoimmune Atrophic Gastritis" *Clinical Gastroenterology and Hepatology*, 2012, pp. 812-814.
Non-Final Office Action for U.S. Appl. No. 16/465,237, filed May 30, 2019, on behalf of SOFAR S.P.A. dated Jul. 9, 2021. 37 Pages.
Non-Final Office Action for U.S. Appl. No. 16/467,797, filed Jun. 6, 2019 on behalf of SOFAR S.P.A. dated Dec. 14, 2021 35 pages.
Notice of Allowance for U.S. Appl. No. 15/305,470, filed Oct. 20, 2016 on behalf of SOFAR S.P.A. dated Jun. 1, 2021 15 pages.
Notice of Allowance for U.S. Appl. No. 15/305,470, filed Oct. 20, 2016, on behalf of SOFAR SPA. dated Nov. 3, 2021. 8 Pages.
Notice of Allowance for U.S. Appl. No. 15/305,470, filed Oct. 20, 2016, on behalf of SOFAR SPA. dated Sep. 8, 2021. 8 Pages.
Notice of Allowance for U.S. Appl. No. 16/301,361, filed Nov. 13, 2018, on behalf of SOFAR S.P.A. dated Aug. 4, 2021. 11 Pages.
Restriction Requirement for U.S. Appl. No. 16/467,797, filed Jun. 7, 2019 on behalf of SOFAR S.P.A. dated Jun. 15, 2021 6 pages.
Rodriguez-Castro K. I. et al., "Clinical manifestations of chronic atrophic gastritis" Acta Biomed, vol. 89, 2018, pp. 88-92.
Salvetti E. et al., "The Genus Lactobacillus: A Taxonomic Update" *Probiotics & Antimicro. Prot.*, Nov. 2012, vol. 4, pp. 217-226.
Scarpignato C. et al., "Management of colonic diverticular disease in the third millennium: Highlights from a symposium held during the United European Gastroenterology Week 2017" Therapeutic Advances in Gastroenterology, vol. 11, Mar. 2018, pp. 1-21.
Tsimmerman Y. S. "Eubiosis and Dysbiosis of Gastrointestinal Tract: Myths and Reality" *Perm State Medical Academy*, 2013, 27 pages.
Wells D. "Gastritis Diet: What to Eat and What to Avoid" Healthline, Jul. 2020, 11 pages.
World Gastroenterology Organisation Global Guidelines "Probiotics and prebiotics" Feb. 2017, 35 pages.
Zhang, Z., et al., "Isolated exopolysaccharides from Lactobacillus rhamnosus GG alleviated adipogenesis mediated by TLR2 in mice," *Sci Rep* 6, 36083, Oct. 27, 2016. 13 Pages. https://doi.org/10.1038/srep36083.
Brussow H. "Problems with the concept of gut microbiota dysbiosis" Microbial Biotechnology, vol. 13(2), 2020, pp. 423-434.
Koebnick C. et al., "Probiotic beverage containing Lactobacillus casei Shirota improves gastrointestinal symptoms in patients with chronic constipation" Can J Gastroenterol, vol. 17 No. 11, Nov. 2003, pp. 655-658.
Non-Final Office Action for U.S. Appl. No. 14/916,959, filed Mar. 4, 2016 on behalf of SOFAR S.P.A. dated Apr. 13, 2021 33 pages.
Non-Final OfficeAction for U.S. Appl. No. 16/308,330, filed Dec. 7, 2018 on behalf ofSOFAR S.P.A. dated Apr. 30, 2021. 38 Pages .
Notice of Allowance for U.S. Appl. No. 16/301,361, filed Nov. 13, 2018 on behalf of SOFAR S.P.A. dated May 3, 2021 9 pages.
Tuohy K.M. et al., "Survivability of a probiotic Lactobacillus casei in the gastrointestinal tract of healthy human volunteers and its impact on the faecal microflora" *Journal of Applied Mircrobiology*, 2007, pp. 1026-1032.
Azad M.D.A.K et al., "Immunomodulatory Effects of Probiotics on Cytokine Profiles" Biomed Research International, vol. 2018, Article ID 8063647, Oct. 2018, pp. 1-10.
Bedford A. et al., "Implications of butyrate and its derivatives for gut health and animal production" *Animal Nutrition*, vol. 4, 2018, pp. 151-159.
Borycka-Kiciak K. et al., "Butyric acid—a well-known molecule revisited" *Gastroenterology Rev*, vol. 12 No. 2, 2017, pp. 83-89.

(56) References Cited

OTHER PUBLICATIONS

Brunkwall L. et al., "Self-reported bowel symptoms are associated with differences in overall gut microbiota composition and enrichment of Blautia in a population-based cohort" *Journal of Gastroenterology and Hepatology*, vol. 36, (2021), pp. 174-180.

Cheng A. et al., "Polyphenols from blueberries modulate inflammation cytokines in LPS-induced RAW264.7 macrophages", *International Journal of Biological Macromolecules*, Elsevier vol. 69, Jun. 2014, pp. 382-387.

Cicenia, A. et al., "Postbiotic Activities of Lactobacilli-derived Factors", J Clin Gastroenterol, vol. 48, Supp. 1, Nov./Dec. 2014, S18-S22 (5 pages).

Connors J. et al., "The Role of Succinate in the Regulation of Intestinal Inflammation" *Nutrients*, vol. 11 No. 25, 2019, 12 pages.

Corrected Notice of Allowability for U.S. Appl. No. 15/305,470, filed Oct. 20, 2016, on behalf of SOFAR SPA. dated Feb. 25, 2022. 3 Pages.

Corrected Notice of Allowability for U.S. Appl. No. 16/465,237, filed May 30, 2019, on behalf of SOFAR S.P.A. dated Jun. 22, 2022. 20 Pages.

Cui J. et al., "NMR-based metabonomics and correlation analysis reveal potential biomarkers associated with chronic atrophic gastritis" *Journal of Pharmaceutical and Biomedical Analysis*, vol. 132, 2017, pp. 77-86.

De Almada C. N. et al., "Paraprobiotics: Evidences on their ability to modify biological responses, inactivation methods and perspectives on their application in foods" *Trends in Food Science & Technology*, vol. 58, 2016, pp. 96-114.

Feng W. et al., "Sodium Butyrate Attenuates Diarrhea in Weaned Piglets and Promotes Tight Junction Protein Expression in Colon in a GPR109A-Dependent Manner" *Cellular Physiology and Biochemistry*, vol. 47, 2018, pp. 1617-1629.

Gwiazdowska D. et al., "The impact of polyphenols on Bifidobacterium growth", Acta Biochimica Polonica, vol. 62 No. 4, Jan. 2015, 895-901. 8 pages.

Hajjar R. et al., "The role of butyrate in surgical and oncological outcomes in colorectal cancer" *American Journal of Physiology*, vol. 320, Jan. 2021, pp. G601-G608.

Hakansson A. et al., "Blueberry husks, rye bran and multi-strain probiotics affect the severity of colitis induced by dextran sulphate sodium" *Scandinavian Journal of Gastroenterology*, vol. 44 No. 10, Jan. 2009, pp. 1213-1225.

Hurst N.R et al., "The Short Chain Fatty Acids, butyrate and Propionate, have Differential Effects on the Motility of the Guinea Pig Colon" *Neurogastroenterol Motil.*, vol. 26 No. 11, Nov. 2014, pp. 1586-1596.

International Preliminary Report on Patentability for International Application No. PCT/IB2020/058774 filed on Sep. 21, 2020 on behalf of SOFAR S.P.A. dated Mar. 15, 2022 16 pages.

International Preliminary Report on Patentability for International Application No. PCT/IB2020/058769 filed on Sep. 21, 2020 on behalf of SOFAR S.P.A. dated Mar. 15, 2022 6 pages.

International Preliminary Report on Patentability for International Application No. PCT/IB2020/058777 filed on Sep. 21, 2020 on behalf of SOFAR S.P.A. dated Mar. 15, 2022 6 pages.

International Preliminary Report on Patentability for International Application No. PCT/IB2020/058778 filed on Sep. 21, 2020 on behalf of SOFAR S.P.A. dated Mar. 15, 2022 6 pages.

International Preliminary Report on Patentability for International Application No. PCT/IB2020/060412 filed on Nov. 5, 2020 on behalf of SOFAR S.P.A. dated May 10, 2022 7 pages.

International Search Report and Written Opinion for International Application No. PCT/IB2020/058778 filed on Sep. 21, 2020 on behalf of SOFAR S.P.A. dated Feb. 18, 2021 8 pages.

International Search Report and Written Opinion for International Application No. PCT/IB2020/058769 filed on Sep. 21, 2020 on behalf of SOFAR S.P.A. dated Feb. 18, 2021 8 pages.

International Search Report and Written Opinion for International Application No. PCT/IB2020/058774 filed on Sep. 21, 2020 on behalf of SOFAR S.P.A. dated Dec. 8, 2020 8 pages.

International Search Report and Written Opinion for International Application No. PCT/IB2020/058777 filed on Sep. 21, 2020 on behalf of SOFAR S.P.A. dated Apr. 20, 2021 26 pages.

International Search Report and Written Opinion for International Application No. PCT/IB2020/060412 filed on Nov. 5, 2020 on behalf of SOFAR S.P.A. dated Mar. 4, 2021 10 pages.

Koradia P. et al., "Probiotic and cranberry supplementation for preventing recurrent uncomplicated urinary tract infections in premenopausal women: a controlled pilot study" *Expert Review of Anti-Infective Therapy*, vol. 17 No. 9, Sep. 2019, pp. 733-740.

Krokowicz L. et al., "Sodium butyrate and short chain fatty acids in prevention of travellers, diarrhoea—a randomized prospective study" *Travel Medicine and Infectious Disease*, Aug. 2013, 17 pages.

Lacombe A. et al., "The potential of berries to serve as selective inhibitors of pathogens and promoters of beneficial microorganisms" *Food Quality and Safety*, vol. 1 No. 1, Mar. 2017, pp. 3-12.

Le Noci V. et al., "Modulation of Pulmonary Microbiota by Antibiotic or Probiotic Aerosol Therapy: A Strategy to Promote Immunosurveillance against Lung Metastases" *Cell Reports*, vol. 24 No. 13, Sep. 2018, pp. 3528-3538.

Lee Y. K. et al., "Handbook of Probiotics and Prebiotics" Wiley, 2009, Excerpt: 3 pages.

Metagenomics—Wikipedia, the free encyclopedia, Dated: May 16, 2013 https://web.archive.org/web/20130516095714/https://en.wikipedia.org/wiki/Metagenomics , 16 pages.

Mileo A.M. et al., "Polyphenols: Immunomodulatory and Therapeutic Implication in Colorectal Cancer" *Frontiers in Immunology*, vol. 10, article 729 Apr. 2019, 10 pages.

Milko Radicioni, et al., "Survival of L. casei DG (CNCMI1572) in the gastrointestinal tract of a healthy paediatric population", *European Journal of Nutrition, Steinkopff Verlag*, vol. 58 No. 8, Nov. 2018, 3161-3170. 10 pages.

Nanau R.M. et al., "Nutritional and Probiotic Supplementation in Colitis Models" *Digestive Diseases and Sciences, Kluwer Academic Publishers-Plenum Publishers*, vol. 57 No. 11, Jun. 2012, pp. 2786-2810.

Notice of Allowance for U.S. Appl. No. 15/305,470, filed Oct. 20, 2016 on behalf of SOFAR S.P.A. dated Feb. 15, 2022 6 pages.

Notice of Allowance for U.S. Appl. No. 15/305,470, filed Oct. 20, 2016, on behalf of SOFAR SPA. dated Jun. 9, 2022. 11 Pages.

Notice of Allowance for U.S. Appl. No. 16/301,361, filed Nov. 13, 2018, on behalf of SOFAR S.P.A. dated Mar. 30, 2022. 11 Pages.

Notice of Allowance for U.S. Appl. No. 16/465,237, filed May 30, 2019, on behalf of SOFAR S.P.A. dated Jun. 1, 2022. 15 Pages.

Notice of Allowance for U.S. Appl. No. 16/467,797, filed Jun. 7, 2019 on behalf of SOFAR S.P.A. dated Jul. 15, 2022 13 pages.

Patel R. M. et al., "Therapeutic Use of Prebiotics, Probiotics, and Postbiotics to Prevent Necrotizing Enterocolitis: What is the Current Evidence?" *Clin Perinatol*, vol. 40, Mar. 2013, pp. 1-20.

Poortmans J. R. et al., "Protein metabolism and physical training: any need for amino acid supplementation?" *Nutrire*, vol. 41 No. 21, 2016, pp. 1-17.

Qin J. et al., "A human gut microbial gene catalogue established by metagenomic sequencing" *Nature*, vol. 46, Mar. 2010, pp. 59-67.

Rajendran V.M. et al., "Na-H Exchanger Isoform-2 (NHE2) Mediates Butyrate-dependent Na+ Absorption in Dextran Sulfate Sodium (DSS)-induced Colitis" *Journal of Biological Chemistry*, vol. 290 No. 42, Oct. 2015, 25487-25496. 10 pages.

Saez-Lara M.J. et al., "The Role of Probiotic Lactic Acid Bacteria and Bifidobacteria in the Prevention and Treatment of Inflammatory Bowel Disease and Other Related Diseases: A systematic review of randomized human clinical trials" *Biomed Research International*, vol. 2015, article ID 505878 Jan. 2015, pp. 1-15.

Santigosa E. et al., "Modifications of intestinal nutrient absorption in response to dietary fish meal replacement by plant protein sources in sea bream (*Sparus aurata*) and rainbow trout (*Onchorynchus mykiss*)" *Fish Nutrition Research Laboratory*, 2011, 38 pages.

Tomar S. K. et al., "Role of probiotics, prebiotics, synbiotics, and postbiotics in inhibition of pathogens" *The Battle Against Microbial Pathogens: Basic Science, Technological Advances and Educational Programs*, 2015, pp. 717-732.

Tsilingiri K. et al., "Postbiotics: what else?" *Beneficial Microbes*, vol. 4 No. 1, Mar. 2013, pp. 101-107 (Abstract Only).

(56) References Cited

OTHER PUBLICATIONS

Tsilingiri, K. et al., "Probiotic and postbiotic activity in health and disease: activity comparison on a novel polarised ex-vivo organ culture method", Gut 2012; 61:1007-1015 (9 pages).

Vicariotto, Franco "Effectiveness of an association of a cranberry dry extract, D-mannose, and the two microorganisms Lactobacillus plantarum LP01 and Lactobacillus paracasei LPC09 in women affected by cystitis: a pilot study." *J Clin Gastroenterol*, Nov. 2014, vol. 48, Supp. 1,: S96-S101. 6 pages.

WHO Technical Report Series 935—Protein and Amino Acid Requirements in Human Nutrition, 2007, 284 pages.

Xu J. et al., "Intake of blueberry fermented by lactobacillus plantarum affects the guy microbiota of L-name treated rats" *Evidence-Based Complementary and Alternative Medicine*, vol. 2013, article ID 809128, Jan. 2013, pp. 1-9.

Xue H. Lactose-Induced Chronic Diarrhea Results from Abnormal Luminal Microbial Fermentation and Disorder of Ion Transport in the Colon *Frontiers in Physiology*, vol. 11, article 877, Jul. 2020, pp. 1-14.

Yehua Yan, et al., "Mixed fermentation of blueberry pomace with L. rhamnosus GG and L. plantarum-1: Enhance the active ingredient, antioxidant activity and health-promoting benefits", *Food and Chemical Toxicology*, vol. 131, 2019, 8 pages.

Yoshida Y. et al., "Oral administration of Lactobacillus plantarum Lq80 and Megasphaera elsdenii iNP-001 induces efficient recovery from mucosal atrophy in the small and the large intestines of weaning piglets" *Animal Science Journal*, vol. 80, 2009, pp. 709-715.

Zhernakova A. et al., "Population-based metagenomics analysis reveals markers for gut microbiome composition and diversity" Science, vol. 352, Apr. 2016, 15 pages.

Canadian Office Action for CA Application No. 2,923,390 filed on Sep. 5, 2014 on behalf of SOFAR S.P.A. dated Nov. 29, 2021 5 pages.

Chinese Office Action for CN Application No. 201780029401.1 filed on May 15, 2017 on behalf of SOFAR S.P.A. dated Dec. 15, 2021 (English + Original) 24 pages.

Colombian Office Action for CO Application No. NC2018/0010950 filed on May 15, 2017 on behalf of SOFAR S.P.A. dated Oct. 14, 2021 (Partial English + Original) 9 pages.

Corrected Notice of Allowability for U.S. Appl. No. 15/305,470, filed Oct. 20, 2016 on behalf of SOFAR S.P.A. dated Jan. 10, 2022 4 pages.

Final Office Action for U.S. Appl. No. 16/308,330, filed Dec. 7, 2018, on behalf of SOFAR S.P.A. dated Feb. 9, 2022. 22 Pages.

Mexican Office Action for MX Application No. MX/a/2016/022766 filed on Sep. 5, 2014 on behalf of SOFAR S.P.A. dated Oct. 26, 2021 (Partial English + Original) 12 pages.

Patel, R., et a., "New Approaches for Bacteriotherapy: Prebiotics, New-Generation Probiotics, and Synbiotics," *Clinical Infectious Diseases*, vol. 60, Issue supplement 2, May 15, 2015. pp. S108-S121. 15 Pages, https://doi.org/10.1093/cid/civ177.

Yuanning S. et al., "Analysis of Lactic Acid Bacteria Protein Dissolution and Aroma Production Ability" Chinese Brew, vol. 33 No. 3, Dec. 31, 2014 (English Abstract + Original) 4 pages.

\* cited by examiner

| Selection and consent | Reference test | | Day 15 |
|---|---|---|---|
| Selection | Height and weight | | Height and weight |
| Informed consent | Vital signs | | Supplement compliance control |
| Demography | Supplement administration instructions | 2 weeks of administration of the supplement + recording of the diet | Diet recording control |
| Anamnesis | | | Fasting blood draw |
| Physical activity | Diet recording instructions | | Ingestion of dietary supplement (animal or plant protein) with/without a probiotic |
| Height and weight | Dietary restrictions | | Subsequent blood draws (30, 60, 120, 180 minutes) |
| Vital signs | | | Scheduled control visit |
| Randomisation | Experimental tests scheduling | | |

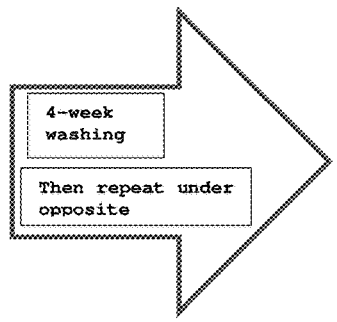

4-week washing

Then repeat under opposite

COMPOSITIONS COMPRISING BACTERIAL STRAINS FOR USE IN INCREASING THE BIOAVAILABILITY OF AMINO ACIDS DERIVED FROM PROTEINS, AND RELATED FOOD PRODUCT METHODS AND SYSTEMS

CROSS-REFERENCE TO RELATED APPLICATIONS

The present disclosure claims priority to US provisional application entitled "Composizioni comprendenti ceppi di batteri per uso per aumentare la biodisponibilita degli amminoacidi derivanti da proteine" filed on Nov. 5, 2019 as U.S. provisional No. 62/930,785 and to Italian patent application no. 102019000020422 filed on Nov. 5, 2019 entitled "Composizioni comprendenti ceppi di batteri per uso per aumentare la biodisponibilita degli amminoacidi derivanti da protein", the disclosure of each of which is incorporated herein by reference in its entirety. The present application is also related to PCT application entitled "Compositions comprising bacterial strains for use in increasing the bioavailability of amino acids derived from proteins" filed on Nov. 5, 2020 as PCT application No. PCT/IB2020/060412 the disclosure of which is also incorporated by reference in its entirety.

FIELD

The present disclosure relates to bacteria and bioavailability of macromolecules. In particular, the present disclosure relates to compositions comprising bacterial strains for use in increasing the bioavailability of amino acids derived from proteins and related food products methods and systems.

BACKGROUND

Proteins are macromolecules which provide important macronutrients absorbed by the digestive tract of an individual.

Challenges however remain in obtaining a desired bioavailability and blood absorption of amino acids from proteins in an individual.

SUMMARY

The present disclosure relates to compositions for use in increasing the blood bioavailability of amino acids derived from proteins, preferably proteins of plant origin, wherein said compositions comprise a mixture M comprising, or alternatively, consisting of at least one bacterial strain, preferably *Lactobacillus paracasei* DG® CNCM I-1572 and/or *Lactobacillus paracasei* LPC-S01™ DSM 26760 (for example, AminoAlta™, trademark registered by Sofar S.p.a., Italy).

Furthermore, the present disclosure relates to said compositions for use further comprising at least one protein, preferably proteins of plant origin, or a peptide or an amino acid.

Lastly, the present disclosure relates to a food product comprising proteins, preferably of plant origin, and said mixture M comprising or, alternatively, consisting of at least one bacterial strain, preferably *Lactobacillus paracasei* DG® CNCM I-1572 and/or *Lactobacillus paracasei* LPC-S01™ DSM 26760.

Accordingly, the present disclosure relates to compositions and related food products method and systems for use in increasing the blood bioavailability of amino acids derived from proteins, preferably proteins of plant origin, comprising a mixture M comprising or, alternatively, consisting of at least one bacterial strain, preferably *Lactobacillus paracasei* DG® CNCM I-1572 and/or *Lactobacillus paracasei* LPC-S01™ DSM 26760, In embodiments of compositions food products, methods and systems herein described mixture M can be comprised in combination with at least one protein, preferably proteins of plant origin, a peptide and/or an amino acid, Embodiments here described comprise, in particular, a food product comprising proteins, preferably of plant origin, and said mixture M of at least one bacterial strain.

The details of one or more embodiments of the disclosure are set forth in the accompanying drawings and the description below. Other features, objects, and advantages will be apparent from the description and drawings, and from the claims.

BRIEF DESCRIPTION OF THE FIGURE

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 1: detailed diagram of the clinical trial.

DETAILED DESCRIPTION

Proteins are an essential part of living organisms and they are formed by the union of simpler molecules called amino acids which bind to each other through peptide bonds. Through several reactions, our organism is capable of autonomously synthesising the proteins it needs starting from the individual amino acids contained in food. Many proteins are part of the category of enzymes, whose function is to catalyse the biochemical reactions vital to the metabolism of organisms. Some have structural and mechanical functions, such as actin and myosin in muscles, collagen in bones and tissues, and as components of cell cytoskeleton. Other proteins are important mediators in the transmission of inter- and intra-cellular signals, in immune response, in cell adhesion mechanisms, in the cell-division cycle.

Since proteins cannot be absorbed as such and transported in circulation, some enzymes present in the lumen of the gastrointestinal tract intervene in their digestion breaking them down into individual amino acids. During the digestive process, most proteins are completely reduced into the individual amino acids. Digestion of these macromolecules begins in the stomach, where the combined action of pepsinogen and hydrochloric acid leads to the formation of oligopeptides (short amino acid chains formed by less than ten units). Such digestion is then completed by intestinal proteases of pancreatic origin, which can be divided into endopeptidases and exopeptidases. Specifically, the aforementioned digestion of proteins is completed at the intestinal level thanks to the action of the exopeptidases present in the microvilli of the small intestine, which lead to the formation of the individual amino acids, dipeptides and tripeptides, which can thus be absorbed at the mucosal level by means of a Na+ or H+ symport mechanism.

The intestinal bacterial flora present at the level of the small intestine, especially lactobacilli, also contributes to further digest the peptides, also acting on those not completely hydrolysed by the protease. Only a small amount of the peptides ingested, equal to about 5%, reaches the colon, where it is subjected to the action of the resident bacterial flora (lactobacilli and bifidobacteria).

Once absorbed, the individual amino acids are transported to the liver by specific carriers, and in this case, they can: be used as such and intervene in the immune response, in the synthesis of hormones and vitamins, in the transmission of nerve impulses, in the production of energy and as catalysts in many metabolic processes; participate in protein synthesis, an process inverse to the digestive process that aims at providing the organism with materials for the growth, maintenance and reconstruction of cell structures; if present in excess it can be used for energy purposes (gluconeogenesis) or converted into deposit fat.

The human body breaks down proteins daily, synthesising others. This process is defined as protein turnover. With normal protein intake, only 4% of the proteins turned over may be lost. This situation can be controlled by protein intake, therefore by a high or low supply of daily proteins. The nitrogen balance compares the amount of nitrogen (from food proteins) introduced into the body with the nitrogen being lost. If a person takes more nitrogen than lost, it is said that it results in a positive nitrogen balance, and it deposits nitrogen in the body. If a person takes the same amount of nitrogen as lost, it is said that it results in a balanced nitrogen balance situation, while if a person loses more nitrogen than taken, this is the case of negative nitrogen balance and loses body proteins.

Protein requirement is defined as the amount of food proteins needed to compensate for and equate the loss of nitrogen on a daily basis, so that a person maintains the nitrogen balance. In other words, protein requirement is the amount of protein our body needs to meet its energy needs and maintain good health. These amounts vary depending on some factors such as: age, sex, health condition, work activity or sports activity. The average protein requirement of a person is inversely proportional to age. For example: about 2 g/kg/day in the neonate, about 1.5 g/kg/day at 5 years, and about 1.2 g/kg/day in adolescent-adult age.

Mild protein deficiency can cause: decrease in metabolic efficiency (for example, ease of bleeding, slow wound healing, etc.), decrease in corpusculated elements in the blood, weight loss (as a result of muscle decrease), decrease in muscle volumes, early fatigue, difficulty in concentrating and difficulty in learning, bad mood, muscle and/or joint and/or bone pain, glycemic changes, increased susceptibility to infections. Less frequently, mild protein deficiency can also cause: anxiety (due to the altered synthesis of neurotransmitters), decrease in athletic performance (decrease in compensation of the training stimulus), changes in sleep (some hypothesise that it may be caused by the change in tryptophan and serotonin synthesis), digestive deficiency (proteins allow the natural synthesis of digestive enzymes).

Furthermore, a protein deficiency can generate more serious symptoms or disorders or diseases, such as muscle depletion (consisting of the auto-digestion of muscle proteins to produce energy), decrease in muscle mass and strength and severe decrease in all protein-based components of the organism such as nails, hair, skin, enzymes, neurotransmitters, hormones, immunoglobulins.

A protein is digestible if a high proportion of its amino acids reach the cells of the organism so that they can synthesize the proteins they need.

However, not all proteins are used equally well by the organism, and the bioavailability of the proteins varies depending on the protein source. As a matter of fact, almost 100% of animal proteins is subject to intestinal absorption, whereas plant proteins have a much lower absorption: 52% for lentils, 70% for chickpeas and 36% for wheat.

Furthermore, unlike animal proteins, most plant proteins, such as pea protein, are incomplete because of their low methionine content, and in particular the pea protein contains lower amounts of branched chain amino acids (BCAAs), which play a crucial role in muscle health. Furthermore, plant proteins contain less leucine, one of the essential amino acids for muscle health. This amino acid is particularly important for the activation of muscle protein synthesis. Lastly, it should be pointed out that proteins of plant origin differ in the absorption kinetics and in the amount of amino acids absorbed.

There is currently observed in the population a high consumption of proteins of plant origin, both for ethical reasons and for health reasons, and/or a low consumption of proteins of animal origin. This increased consumption of proteins of plant origin or, in general, a low consumption of proteins of animal origin often does not allow the subject to meet the needed average daily protein requirement.

Furthermore, living conditions that require high protein requirement, such as for example sports activity or pregnancy or breastfeeding, or particular health conditions may require an increased average daily protein requirement of the subject.

Document US2019/0192590 describes the use of probiotic bacterial strains to increase the absorption or the bioavailability of proteins in subjects in need. However, US2019/0192590 neither describes nor discloses an increase in the blood bioavailability of at least one amino acid derived from a protein, even less from a protein of plant origin.

The need therefore remains high to provide an effective solution to meet the average daily protein requirement, in particular, in diets with consumption of proteins mainly of plant origin which have a low degree of absorption. In other words, there arises the need for increasing or enhancing the gastrointestinal absorption of proteins and/or protein derivatives, in particular proteins of plant origin, and/or the blood bioavailability of the amino acids derived from said proteins. This need is felt with reference—particularly but not exclusively—to subjects suffering from diseases, disorders and/or symptoms associated with or derived from a protein deficiency, or to subjects in need of a high average protein requirement as well as subjects such as sportsmen/sportswomen, vegetarians and vegans.

In other words, there is a strong interest in the search for nutritional strategies that allow increasing the concentration of amino acids in the blood after ingesting a source of plant proteins, thus allowing to overcome compositional deficiencies.

Such need is even higher in subjects suffering from diseases, disorders and/or symptoms associated with or derived from a protein deficiency or in subjects in need of a high daily average protein need due to their physical condition or physical activity, such as sports subjects, people subjected to high physical stress, subjects with high physical stress, pregnant or breast-feeding women, subjects of geriatric or paediatric age.

Following extensive research and development activity, the Applicant, addresses and solves the aforementioned needs by providing bacterial strains, compositions comprising bacterial strains or food products comprising bacterial strains capable of increasing the gastrointestinal absorption of proteins, preferably proteins of plant origin, and/or the blood bioavailability of amino acids derived from said proteins, in subjects in need, as reported in the present description and in the claims.

Advantageously, the Applicant found that the supplementation of specific probiotics according to the present disclosure allows increasing the blood absorption and bioavailability of amino acids from proteins, preferably derived from plant proteins.

Advantageously, the bacterial strains, the mixtures, the compositions and the food products of the disclosure allow increasing the concentration of amino acids in the blood after ingesting a source of plant proteins, thus allowing to overcome compositional deficiencies.

Advantageously, the bacterial strains, mixtures, compositions and food products of the disclosure allow a higher blood level of amino acids in a subject considering the same intake of proteins and/or protein derivatives, preferably proteins of plant origin.

Advantageously, the bacterial strains, the mixtures, the compositions and the food products of the disclosure allow to obtain an increase in the maximum concentration (Cmax) and AUC of amino acids, preferably of methionine, histidine, valine, leucine, isoleucine, tyrosine, total BCAAs and maximum concentrations of total EAAs without changing the time required to reach these concentrations (Tmax).

Advantageously, the administration of the bacterial strains, of the mixtures, of the compositions and of the food products of the disclosure represents an important nutritional strategy for enhancing postprandial changes in blood amino acids and for overcoming the compositional deficiencies of plant proteins.

Advantageously, the bacterial strains, the mixtures, the compositions and the food products of the disclosure allow a lower consumption of proteins and/or protein derivatives, preferably proteins of plant origin, by a subject to obtain the same protein intake, with the ensuing cost-effectiveness.

Furthermore, the bacterial strains, the mixtures the compositions and food products of the disclosure do not have significant adverse effects and they can be administered to all subjects, particularly even to paediatric subjects, the elderly, pregnant and breastfeeding women.

Lastly, the compositions of the disclosure and the products of the disclosure are effective, easy to prepare and cost-effective.

These and other objects which will be clearer from the detailed description that follows are achieved by the bacterial strain, by the mixtures and by the compositions of the present disclosure thanks to the technical characteristics claimed in the attached claims.

Forming an object of the present disclosure is an isolated bacterial strain, or a derivative thereof, for use in increasing the gastrointestinal absorption and/or bioavailability of at least one amino acid derived from a protein of animal or plant origin, preferably a protein of plant origin, in a subject taking—through oral route—said protein, preferably said protein of plant origin, or said at least one amino acid or a peptide comprising said at least one amino acid, wherein said bacterial strain (in short, bacterial strain for use of the disclosure or a bacterial strain (I) or (I)) is preferably selected from the group comprising or, alternatively, consisting of:

(I.i) a bacterial strain belonging to the species *Lactobacillus paracasei* identified as *Lactobacillus paracasei* DG® (trademark registered by SOFAR S.p.A.) and deposited at the National Collection of Cultures of Microorganisms of the Pasteur Institute in Paris under accession number CNCM I-1572 on 5 May 1995 by SOFAR S.p.A. (in short, DG® or *L. paracasei* DG® CNCM I-1572 or (I.i)); said strain was initially named *Lactobacillus casei* DG® sub. *casei*; it was subsequently reclassified as *Lactobacillus paracasei* DG®CNCM I-1572: it should be observed that it is still and exclusively the same bacterial strain irrespective of the name *Lactobacillus casei* DG® or *Lactobacillus paracasei* DG®; and (I.ii) a bacterial strain belonging to the species *Lactobacillus paracasei* identified as *Lactobacillus paracasei* LPC-S01™ and deposited at Deutsche Sammlung von Mikroorganismen und Zellkulturen GmbH (DSMZ) under accession number DSM 26760, on 20 Nov. 2012 by SOFAR S.p.A. (in short, LPC-S01™ or *L. paracasei* LPC-S01™ DSM 26760 or (I.ii));

(I.iii) a bacterial strain belonging to the species *Bifidobacterium breve* identified as *Bifidobacterium breve* BbIBS01, or a derivative thereof, wherein said bacterial strain was deposited, according to the Budapest Treaty, at Deutsche Sammlung von Mikroorganismen und Zellkulturen GmbH (DSMZ) under deposit number DSM 33231 on 31 Jul. 2019 by Sofar S.p.A.;

(I.iv) a bacterial strain belonging to the species *Bifidobacterium breve* identified as *Bifidobacterium breve* BbIBS02, or a derivative thereof, wherein said bacterial strain was deposited at Deutsche Sammlung von Mikroorganismen und Zellkulturen GmbH (DSMZ) under deposit number DSM 33232 on 31 Jul. 2019 by Sofar S.p.A.;

(I.v) a bacterial strain belonging to the species *Bifidobacterium animalis* identified as *Bifidobacterium animalis* subsp. *lactis* BlIBS01, or a derivative thereof, wherein said bacterial strain was deposited at Deutsche Sammlung von Mikroorganismen und Zellkulturen GmbH (DSMZ) under deposit number DSM 33233 on 31 Jul. 2019 by Sofar S.p.A.;

(I.vi) a bacterial strain belonging to the species *Lactobacillus plantarum* identified as *Lactobacillus plantarum* LpIBS01, or a derivative thereof, wherein said bacterial strain was deposited at Deutsche Sammlung von Mikroorganismen und Zellkulturen GmbH (DSMZ) under deposit number DSM 33234 on 31 Jul. 2019 by Sofar S.p.A.; and a mixture thereof.

The term "an isolated bacterial strain" is used to indicate a bacterial strain isolated according to standard techniques known to the man skilled in the art.

Forming an object of the present disclosure is a composition for use in increasing the blood bioavailability of at least one amino acid derived from a protein of plant or animal origin, preferably from a protein of plant origin, in a subject taking—through oral route—said protein or said at least one amino acid or a peptide of plant origin comprising said at least one amino acid, wherein said composition comprises a mixture M comprising, or alternatively, consisting of at least one bacterial strain, or a derivative thereof, selected from the group comprising, or alternatively, consisting of:

a bacterial strain belonging to the species *Lactobacillus paracasei* identified as *Lactobacillus paracasei* DG® and deposited at the National Collection of Cultures of Microorganisms of the Pasteur Institute in Paris under the accession number CNCM I-1572, a bacterial strain belonging to the species *Lactobacillus paracasei* identified as *Lactobacillus paracasei* LPC-S01™ and deposited at Sammlung von Mikroorganismen und Zellkulturen GmbH (DSMZ) under accession number DSM 26760, a bacterial strain belonging to the species *Bifidobacterium breve* identified as *Bifidobacterium breve* BbIBS01 and deposited at Deutsche Sammlung von Mikroorganismen und Zellkulturen GmbH (DSMZ) under deposit number DSM 33231, a bacterial strain belonging to the species *Bifidobacterium breve* identified as *Bifidobacterium breve* BbIBS02 and deposited at Deutsche Sammlung von Mikroorganismen und Zellkulturen GmbH (DSMZ) under deposit number DSM 33232, a bacterial strain belonging to the species *Bifidobacterium animalis* identified as *Bifidobacterium animalis* subsp. *lactis* BIIBS01 and deposited at Deutsche Sammlung von Mikroorganismen und Zellkulturen GmbH (DSMZ) under deposit number DSM 33233, a bacterial strain belonging to the species *Lactobacillus plantarum* identified as *Lactobacillus plantarum* LpIBS01 and deposited at Deutsche Sammlung von Mikroorganismen und Zellkulturen GmbH (DSMZ) under deposit number DSM 33234, and a mixture thereof; and, optionally, said composition comprises at least one acceptable pharmaceutical or food grade additive and/or excipient, wherein said at least one amino acid is selected from the group A comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof, and wherein, said increase in the blood bioavailability of said at least one amino acid (expressed as a statistically significant increase in AUC or Cmax) is comprised, preferably from +2% to +55%.

Forming an object of the disclosure is a composition (in short, composition of the disclosure) for use in increasing the gastrointestinal absorption and/or the bioavailability of at least one amino acid derived from a protein of animal or plant origin, preferably a protein of plant origin, in a subject taking—through the oral route—said protein, preferably a protein of plant origin or said at least one amino acid or a peptide comprising said at least one amino acid, wherein said composition comprises a mixture M (in short, mixture M of the disclosure) comprising or, alternatively, consisting of at least one bacterial strain, or a derivative thereof, selected from the group comprising or, alternatively, consisting of: (I.i) *Lactobacillus paracasei* DG® CNCM I-1572, (I.ii) *Lactobacillus paracasei* LPC-S01™ DSM 26760, (I.iii) *Bifidobacterium breve* BbIBS01 DSM 33231, (I.iv) *Bifidobacterium breve* BbIBS02 DSM 33232, (I.v) *Bifidobacterium animalis* subsp. *lactis* BIIBS01 DSM 33233, (I.vi) *Lactobacillus plantarum* LpIBS01 DSM 33234 and a mixture thereof;

and, optionally, said composition comprises at least one acceptable pharmaceutical or food grade additive and/or excipient.

Furthermore, forming an object of the present disclosure is a mixture comprising or, alternatively, consisting of, (I.i) *Lactobacillus paracasei* DG® CNCM I-1572 (freeze-dried in powder form), (I.ii) *Lactobacillus paracasei* LPC-S01™ DSM 26760 (freeze-dried in powder form), preferably at a 1:1 by weight ratio and, optionally, maltodextrin for use in increasing the blood bioavailability of at least one amino acid derived from a protein of plant or animal origin, preferably from a protein of plant origin, in a subject taking—through oral route—said protein or at least one amino acid or a peptide of plant origin comprising said at least one amino acid.

Furthermore, forming an object of the present disclosure is probiotic bacterial strain (I.i) *Lactobacillus paracasei* DG® CNCM I-1572 (freeze-dried in powder form), for use in increasing the blood bioavailability of at least one amino acid derived from a protein of plant or animal origin, preferably from a protein of plant origin, in a subject taking—through oral route—said protein or said at least one amino acid or a peptide of plant origin comprising said at least one amino acid.

Furthermore, forming an object of the present disclosure is a probiotic bacterial strain (I.ii) *Lactobacillus paracasei* LPC-S01™ DSM 26760 (freeze-dried in powder form), for use in increasing the blood bioavailability of at least one amino acid derived from a protein of plant or animal origin, preferably from a protein of plant origin, in a subject taking—through oral route—said protein or said at least one amino acid or a peptide of plant origin comprising said at least one amino acid.

Furthermore, forming an object of the present disclosure is a non-therapeutic use of the composition according to the present disclosure in increasing the blood bioavailability of at least one amino acid derived from a protein of plant or animal origin, preferably from a protein of plant origin, in a subject taking—through oral route—said protein or said at least one amino acid or a peptide of plant origin comprising said at least one amino acid Furthermore, forming an object of the present disclosure is a method for increasing the blood bioavailability of at least one amino acid derived from a protein of plant or animal origin, preferably from a protein of plant origin, comprising administering the composition according to the present disclosure to a subject taking—through oral route—said protein or at least one amino acid or a peptide of plant origin comprising said at least one amino acid.

In a preferred embodiment of the composition for use of the disclosure, said mixture M comprises or, alternatively, consists of (I.i) *Lactobacillus paracasei* DG® CNCM I-1572, or a derivative thereof, and/or (I.ii) *Lactobacillus paracasei* LPC-S01™ DSM 26760, or a derivative thereof.

In an embodiment of the composition for use of the disclosure, besides at least one bacterial strain, or a derivative thereof, selected from (I.i) *Lactobacillus paracasei* DG® CNCM I-1572, (I.ii) *Lactobacillus paracasei* LPC-S01 DSM 26760 and a mixture thereof, said mixture M further comprises or, alternatively, consists of at least one bacterial strain, or a derivative thereof selected from the group comprising or, alternatively, consisting of: (I.iii) *Bifidobacterium breve* BbIBS01 DSM 33231, (I.iv) *Bifidobacterium breve* BbIBS02 DSM 33232, (I.v) *Bifidobacterium animalis* subsp. *lactis* BIIBS01 DSM 33233, (I.vi) *Lactobacillus plantarum* LpIBS01 DSM 33234, and mixtures thereof.

In a preferred embodiment of the composition for use of the disclosure, besides the bacterial strains, or the derivatives thereof, (I.i) *Lactobacillus paracasei* DG® CNCM I-1572 and (I.ii) *Lactobacillus paracasei* LPC-S01™ DSM 26760, said mixture M further comprises or, alternatively, consists of at least one bacterial strain, or a derivative thereof, selected from the group comprising or, alternatively, consisting of: (I.iii) *Bifidobacterium breve* BbIBS01 DSM 33231, (I.iv) *Bifidobacterium breve* BbIBS02 DSM 33232, (I.v) *Bifidobacterium animalis* subsp. *lactis* BIIBS01 DSM 33233, (I.vi) *Lactobacillus plantarum* LpIBS01 DSM 33234, and mixtures thereof.

In an embodiment of the present disclosure, the mixture contained in the composition for use according to the present disclosure comprises, or alternatively, consists of: (I.i) *Lac-* tobacillus paracasei DG® CNCM I-1572 (freeze-dried in powder form), (I.ii) *Lactobacillus paracasei* LPC-S01™ DSM 26760 (freeze-dried in powder form) at a 1:1 by weight ratio and, optionally, maltodextrin.

In an embodiment of the composition for use of the disclosure, said at least one amino acid, whose blood absorption and/or bioavailability increases due to the effect of said at least one bacterial strain is selected from the group A of amino acids comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

In an embodiment, said increase in the blood bioavailability of said at least one amino acid (expressed as a statistically significant increase in AUC, defined as reported hereinafter in the text) is comprised from +1% to +85%, preferably comprised from +5% to +55%, even more preferably comprised from +15% to +45%, or from 16% to 43%.

In an embodiment, said increase in the blood bioavailability of said at least one amino acid (expressed as a statistically significant increase in Cmax, defined as reported hereinafter in the text) is comprised from +1% to +85%, preferably comprised from +5% to +55%, even more preferably comprised from +15% to +45%, or from 16% to 43%.

Advantageously, said at least one amino acid is selected from the group A.1 of amino acids comprising or, alternatively, consisting of: methionine, histidine, valine, leucine, isoleucine, tyrosine, arginine, cysteine, glycine, glutamine, proline, a mixture of leucine, isoleucine and valine (BCAAs, branched chain amino acids), and a mixture of essential amino acids (EAAs) for humans, consisting of histidine, isoleucine, leucine, lysine, methionine, phenylalanine, threonine, tryptophan, valine.

Advantageously, said increase in blood bioavailability (expressed as statistically significant increase in AUC, defined as reported hereinafter in the text) relates to at least one amino acid selected from group A.1. and it is comprised from +2% to +75%, preferably comprised from +8% to +55%, even more preferably comprised from +15% to +45%, or from 16% to 43%.

Advantageously, said increase in the blood bioavailability (expressed as a statistically significant increase in Cmax, defined as reported hereinafter in the text) relates to at least one amino acid selected from group A.1 and it is comprised from +2% to +85%, preferably from +8% to +55%, even more preferably comprised from +15% to +45%, or 16% to 43%.

Alternatively, said at least one amino acid is selected from the group A.1.a of amino acids comprising or, alternatively, consisting of: methionine, histidine, valine, leucine, isoleucine, tyrosine, aspartic acid, asparagine, alanine, phenylalanine, tryptophan, total BCAAs, total EAAs and mixtures thereof.

In an embodiment, said increase in blood bioavailability (expressed as statistically significant increase in AUC, defined as reported hereinafter in the text) relates to at least one amino acid selected from the group A.1.a and it is comprised from +1% to +85%, preferably from +5% to +45%, even more preferably comprised from +15% to +43%, or from 16% to 41%.

In an embodiment, said increase in the blood bioavailability (expressed as a statistically significant increase in Cmax, defined as reported hereinafter in the text) relates to at least one amino acid selected from group A.1.a and it is comprised from +1% to +85%, preferably from +5% to +45%, even more preferably from +2% to +52%, or from +10% to +50%.

Even more advantageously, said at least one amino acid is selected from the group A.2 of amino acids comprising or, alternatively, consisting of: methionine, histidine, valine, leucine, isoleucine, tyrosine, aspartic acid, total BCAAs, total EAAs and mixtures thereof.

In an embodiment, said increase in blood bioavailability (expressed as statistically significant increase in AUC, defined as reported hereinafter in the text) relates to at least one amino acid selected from group A.2 and it is comprised from +1% to +85%, preferably comprised from +12% to +45%, even more preferably comprised from +15% to +43%, or comprised from +16% to +43%.

In an embodiment, said increase in the blood bioavailability (expressed as a statistically significant increase in Cmax, defined as reported hereinafter in the text) relates to at least one amino acid selected from group A.2 and it is comprised from +1% to +85%, preferably comprised from +10% to +53%, even more preferably comprised from +11% to +50%, or comprised from +16% to +42%. In the context of the present disclosure, the term "increasing gastrointestinal absorption and/or bioavailability of amino acids" is used to indicate the increase blood levels (or serum levels) of one or more amino acids in the subject to whom bacterial strains for use of the disclosure or the composition of the disclosure are administered.

In the present context, the AUC, Cmax and Tmax parameters are used to assess pharmacokinetic behaviour, specifically the pharmacokinetic behaviour of amino acids in blood.

In the context of the present disclosure, AUC is used to indicate the area under the concentration/time curve measured using methods known to the man skilled in the art. This parameter is a commonly used parameter for determining blood bioavailability.

AUC is measured (area under the concentration vs. time curve) for each of the 22 amino acids, as well as for BCAAs, EAAs and total amino acids, using the linear trapezoidal rule and using all available time points. Cmax was defined as the maximum observed concentration and Tmax is the time at which Cmax was reached. AUC values were compared under interpolation conditions by means of paired sample t-tests. A p value<0.05 was considered statistically significant. Results are expressed as mean±standard deviation (SD) unless otherwise specified. In vitro digestion data are the results of three independent determinations, each performed in triplicate. Analysis of data variance was performed using the least significant differences (LSD) test.

In the present context, Cmax is used to indicate the maximum observed concentration at a certain time t. This is measured using methods known to the man skilled in the art.

In the present context, Tmax is used to indicate the time at which a maximum concentration (Cmax) is observed. Tmax is measured using methods known to the man skilled in the art.

Advantageously, the bacterial strains, the mixtures, the compositions and the food products of the disclosure allow to obtain an increase in the Maximum concentration (Cmax) and AUC of the amino acids, without changing the time required to reach such concentrations (Tmax).

Blood bioavailability is expressed as a statistically significant percentage increase in Cmax and/or AUC, and it is defined as the percentage difference measured for each amino acid. Thus, the statistically significant percentage increase intervals of Cmax and/or AUC reported in the present context are to be understood as referring to the single amino acid even if several amino acids are contained in the mixture. For example, in the event of a mixture comprising methionine and histidine the latter may have AUC and Cmax values each comprised within the statistically significant percent increase ranges of Cmax and/or AUC, for example they may be methionine (AUC: +20%, p=0.007; Cmax: +16.3%, p=0.008), histidine (AUC:+40.4%, p=0.009; Cmax: +49.2%, p=0.048).

The blood levels of amino acids are evaluated using analytical methods known to the man skilled in the art. For example, the AUC (area under the curve, as concentration versus time) can be calculated using the linear trapezoidal rule.

Said at least one bacterial strain (I) or a mixture thereof, preferably (I.i) and/or (I.ii), both in the form of strain as such and in the form of composition of the disclosure, enhances the gastrointestinal absorption and/or increase in bioavailability in the amino acid serum levels when administered associated/combined with proteins, preferably of plant origin, or peptides or amino acids, wherein said administration of said one or more bacterial strains (in short, (I)) and of said proteins, preferably of plant origin, or peptides or amino acids (in short, (II)) is simultaneous or delayed over time, preferably simultaneous over time.

In the context of the present disclosure, the expression "simultaneous administration over time" of (I) and (II) is used to indicate that (I) and (II) are administered to said subject approximately at the same period of time, in a single composition or product or by means of two distinct compositions or products, or at a distance of a period of time comprised in the range from 5 minutes to 60 minutes, preferably from 5 minutes to 30 minutes, in any order, preferably first taking (I) and then (II).

In the context of the present disclosure, the expression administration "delayed over time" of (I) and (II) is used to indicate that (I) and (II) are administered to said subject after a period of time from each other by means of two distinct compositions or products, for example at a distance of a period of time comprised in the range from 1 hour to 12 hours, preferably from 1 hour to 6 hours, preferably from 1 hour to 3 hours.

In an embodiment of the composition of the disclosure, besides the mixture M of the disclosure comprising or, alternatively, consisting of at least one at least one bacterial strain (I) selected from the group comprising or, alternatively, consisting of (I.i), (I.ii), (I.iii), (I.iv), (I.v), (I.vi) and mixtures thereof or derivatives thereof, preferably (I.i) and/or (I.ii), said composition further comprises at least one protein of animal or plant origin, preferably of plant origin, and/or at least one peptide, preferably of plant origin and/or at least one amino acid; preferably said at least one amino acid comprised in the composition of the disclosure is selected from group A or group A.1 or A.1.a or group A.2 of amino acids described in the present disclosure.

In an embodiment of said composition of the disclosure, said proteins of plant origin are for example proteins obtained from pea, soy bean or lupine, preferably pea, for example yellow pea (*Pisum sativum*).

Preferably, said at least one bacterial strain (I) or a mixture thereof, preferably (I.i) and/or (I.ii), for use according to the present disclosure, is administered to said subject, both in the form of strain as such and in the form of composition of the disclosure, at a concentration comprised in the range from $10 \times 10^6$ CFU to $10 \times 10^{12}$ CFU, preferably from $10 \times 10^8$ CFU to $10 \times 10^{10}$ CFU, more preferably at a concentration of about $10 \times 10^9$ CFU, with respect to the daily intake (CFU: Colony forming Unit).

In a preferred embodiment of the disclosure, said bacterial strains (I) of the present disclosure, preferably (I.i) and/or (I.ii), both as such and comprised in the composition of the disclosure, are viable bacterial strains, such as, for example, viable bacterial strains present in probiotic products or in Live Biotherapeutic Products (in short, LBP, such as pharmaceutical products comprising viable bacterial strains).

"Probiotics" are live and viable micro-organisms (i.e. bacterial strains) which, when administered in adequate amount, confer benefits to the health of the host; the term "probiotics" refers to micro-organisms present in or added to food (FAO and WHO definition).

In a further embodiment of the disclosure, said bacterial strains (I) of the present disclosure, preferably (I.i) and/or (I.ii), both as such and comprised in the composition of the disclosure, is a derivative of a viable bacterial strain.

In the context of the present disclosure, the term "derivative" of a bacterial strain (or "derivative" of a viable bacterial strain) is used to indicate the bacterial strain tyndallized, or sonicated or inactivated using other techniques known to the man skilled in the art, or lysates of the bacterial strain or extracts of the bacterial strain (paraprobiotics) or any other derivative and/or component of the bacterial strain, preferably exopolysaccharide, parietal fraction, metabolites or metabolic bioproducts generated by the bacterial strain (postbiotics) and/or any other product derived from the bacterial strain. Preferably, the term "derivative" of the bacterial strains of the present disclosure is used to indicate the tyndallized or inactivated bacterial strain.

Forming an object of the disclosure is said composition of the disclosure according to any one of the embodiments of the disclosure, for use in the preventive and/or curative treatment of a protein deficiency or of an increased protein requirement and/or of a disease, symptom and/or disorder associated with said protein deficiency or increased protein requirement, following increase in gastrointestinal absorption and/or bioavailability of said at least one amino acid.

In an embodiment, said bacterial strain of the disclosure (I), preferably (I.i) and/or (I.ii), and said composition of the disclosure according to any one of the embodiments of the disclosure, allow the treatment of diseases, symptoms and/or disorders associated with said protein deficiency or said increased protein requirement selected from: decrease in metabolic efficiency, decrease in corpusculated elements in the blood, changes in healing processes, decrease in muscle strength, decrease in muscle mass, muscle depletion, weight loss, decrease in athletic performance, early fatigue, difficulty in concentrating, anxiety, changes in sleep, changes in mood, increased susceptibility to infections, digestive deficiency, changes in blood sugar, increased cholesterol, changes in blood-chemical parameters, malnutrition syndrome, such as for example Kwashiorkor or biafra, osteoporosis, decrease in at least one protein-based component of an organism selected from nails, hair, skin, enzymes, neurotransmitters, hormones and immunoglobulins, and other disorders or diseases observable from the context of the present disclosure.

In an embodiment, said bacterial strain of the disclosure (I), preferably (I.i) and/or (I.ii), and said composition of the disclosure according to any one of the embodiments of the disclosure, are for use as defined in the present disclosure:
  in subjects with increased protein requirement, or,
  in subjects with protein deficiency disorders, or, in paediatric subjects, preferably paediatric subjects with protein deficiency disorders, or, in pregnant or breastfeeding subjects, preferably pregnant or breastfeeding subjects with protein deficiency disorders, or, in senile-age subjects, preferably senile-age subjects with protein deficiency, or, in vegetarian or vegan subjects, preferably vegetarian or vegan subjects with protein deficiency disorders, or, in subjects receiving therapies which may lead to decrease in protein absorption, or, in subjects with acute or chronic lesions, for example decubitus ulcers, or, in sports subjects.

The composition of the disclosure, comprising said mixture M according to any one of the embodiments of the present disclosure, further optionally it comprises said at least one pharmaceutical or food grade additive and/or excipient, i.e. a substance devoid of therapeutic activity suitable for pharmaceutical or food use. In the context of the present disclosure the additives and/or excipients acceptable for pharmaceutical or food use comprise all ancillary substances known to the man skilled in the art for the preparation of compositions in solid, semi-solid or liquid form, such as for example diluents, solvents (including water, glycerine, ethyl alcohol), solubilisers, acidifiers, thickeners, sweeteners, flavour enhancers, colouring agents, lubricants, surfactants, preservatives, stabilisers, pH stabilising buffers and mixtures thereof.

In an embodiment, besides said mixture M of the disclosure according to any one of the embodiments of the disclosure, and, optionally, at least one protein or peptide or amino acid, the composition of the present disclosure may further comprise at least one further active component selected from the group comprising or, alternatively, consisting of other viable bacterial strains and/or parabiotics and/or postbiotics and/or lysates and/or tyndallized and/or inactivated, enzymes, direct or indirect antacid action substances, prebiotic substances, prebiotic substances belonging to the families of yeasts and bacteria, immunostimulatory substances, antidiarrhoea substances, nutrients, vitamins of group B, C, E, organic and/or inorganic salts of magnesium, of selenium, of zinc, antioxidants, anti-radical agents, minerals, plant extracts (botanicals), soy isoflavones.

Said bacterial strains for use of the disclosure and/or said compositions for use of the disclosure, may be formulated in solid form, such as tablet, chewable tablet, capsule, lozenge, granules, flakes or powder, in semi-solid form, such as soft-gel, cream, or in liquid form, such as solution, suspension, dispersion, emulsion or syrup.

Said bacterial strains for use of the disclosure and/or said compositions of the disclosure, may be formulated for oral (or gastroenteric), sublingual (or buccal), transmucosal, inhalation use (or administration); advantageously they are formulated for oral use, preferably in solid form.

The composition of the disclosure may be a pharmaceutical composition (or Live Biotherapeutic Products), a medical device composition, a dietary supplement, a food or novel food or probiotic product, a composition for a food for special medical purposes.

In the context of the present disclosure, the expression "medical device" is used in the meaning according to the Italian Legislative Decree no 46 dated 24 Feb. 1997 or according to the new Medical Device Regulation (EU) 2017/745 (MDR).

Said bacterial strains of the disclosure or said compositions of the disclosure may also be for use as adjuvants of further therapeutic approaches, preferably of pharmacological or food type, aimed at treating a protein deficiency and related diseases, symptoms and/or disorders.

Forming an object of the present disclosure is a method for the preventive or curative treatment, for increasing the gastrointestinal absorption and/or the bioavailability of at least one amino acid derived from a protein of animal or plant origin, preferably a protein of plant origin, in a subject taking—through oral route said protein, preferably said protein of plant origin, or said at least one amino acid or a peptide comprising said at least one amino acid; in particular for treating diseases, symptoms and/or disorders related with a protein deficiency or related with an increased protein requirement, which provides for the administration—to said subject—a minimum effective amount of at least one bacterial strain (I) of the disclosure, preferably (I.i) and/or (I.ii), or compositions of the disclosure according to any one of the embodiments of the present disclosure.

Forming an object of the present disclosure is the use of at least one bacterial strain (I) of the disclosure, preferably (I.i) and/or (I.ii), or compositions of the disclosure according to any one of the embodiments of the present disclosure, for increasing the gastrointestinal absorption and/or the bioavailability of at least one amino acid derived from a protein, preferably a protein of plant origin, in a subject taking—through oral route—said protein, preferably said protein of plant origin, or said at least one amino acid or a peptide comprising said at least one amino acid; in particular for the preventive or curative treatment of diseases, symptoms and/or disorders related with protein deficiency or related with increased protein requirement, in a subject.

Forming an object of the present disclosure is a food or edible product (in short, food or edible product of the disclosure) comprising proteins of animal or plant origin, preferably proteins of plant origin, and the mixture M of the disclosure according to any one of the embodiments of the disclosure, comprising or, alternatively, consisting of at least one bacterial strain or a derivative thereof, selected from the group comprising or, alternatively, consisting of (I.i), (I.ii), (I.iii), (I.iv), (I.v), (I.vi) and a mixture thereof; preferably *Lactobacillus paracasei* DG® CNCM I-1572 and/or *Lactobacillus paracasei* LPC-S01™ DSM 26760 and, optionally, at least one of (I.iii), (I.iv), (I.v), (I.vi).

In an embodiment of said food or edible product of the disclosure, said proteins of plant origin are for example proteins obtained from pea, soy bean or lupine, preferably pea, for example yellow pea (*Pisum sativum*).

Said food or edible product of the disclosure may be in solid, liquid or semi-solid form. For example, said food product is a hamburger, preferably a hamburger comprising or, alternatively, consisting of plant proteins.

In an embodiment of said food product of the disclosure, said at least one bacterial strain (I), preferably (I.i) and/or (I.ii), is in a form that allows to maintain an effectiveness of the bacterial strain to increase the absorption and/or bioavailability of at least one amino acid comprised in said proteins of plant origin following the processes of production and/or processing the food product (for example cooking or high temperatures in general), wherein said form is selected from among the group comprising or, alternatively, consisting of: coated viable bacterial strain, tyndallized bacterial strain, sonicated bacterial strain, inactivated bacterial strain, lysate of the bacterial strain, extract of the bacterial strain, a component of the bacterial strain selected from exopolysaccharide, parietal fraction, metabolite and metabolic bioproduct, in other words a coated probiotic or a paraprobiotic or a postbiotic.

In an embodiment of the disclosure said food product of the disclosure is for use for increasing the gastrointestinal absorption and/or the bioavailability of at least one amino acid comprised in said protein of plant origin, as described in the present disclosure.

Unless otherwise specified, the expression composition or mixture or other comprising a component at an amount "comprised in a range from x to y" is used to indicate that said component may be present in the composition or mixture or extract or other at all amounts present in said range, even if not specified, extremes of the range comprised.

In the context of the present disclosure, the term "subject/s" is used to indicate human or animal subjects, preferably mammals (e.g. pets such as dogs, cats, horses, sheep or cattle). Preferably, the compositions of the disclosure are for use in treatment methods for human subjects.

As illustrated in detail in the experimental part, administration—to a subject—of at least one bacterial strain (I) according to the disclosure increases serum levels of fundamental amino acids, such as methionine, histidine, valine, leucine, isoleucine, tyrosine, total BCAAs and total EAAs, in a subject to whom proteins of plant origin were administered.

Thus, the administration of a composition according to the disclosure (for example, AminoAlta™) can be an important nutritional strategy to improve protein utilisation and overcome the compositional deficiencies of plant proteins.

Preferred embodiments of the present disclosure FRan are reported below.

FRa1. A composition for use in increasing the blood bioavailability of at least one amino acid derived from a protein of plant origin in a subject who takes said protein of plant origin or said at least one amino acid or a peptide of plant origin comprising said at least one amino acid through oral route, wherein said composition comprises a mixture M comprising, or alternatively, consisting of at least one bacterial strain, or a derivative thereof, selected from the group comprising, or alternatively, consisting of:
  a bacterial strain belonging to the species *Lactobacillus paracasei* identified as *Lactobacillus paracasei* DG® and deposited at the National Collection of Cultures of Microorganisms of the Pasteur Institute in Paris under the accession number CNCM I-1572,
  a bacterial strain belonging to the species *Lactobacillus paracasei* identified as *Lactobacillus paracasei* LPC-S01™ and deposited at Sammlung von Mikroorganismen und Zellkulturen GmbH (DSMZ) under accession number DSM 26760,
  a bacterial strain belonging to the species *Bifidobacterium breve* identified as *Bifidobacterium breve* BbIBS01 and deposited at Deutsche Sammlung von Mikroorganismen und Zellkulturen GmbH (DSMZ) under deposit number DSM 33231,
  a bacterial strain belonging to the species *Bifidobacterium breve* identified as *Bifidobacterium breve* BbIBS02 and deposited at Deutsche Sammlung von Mikroorganismen und Zellkulturen GmbH (DSMZ) under deposit number DSM 33232,
  a bacterial strain belonging to the species *Bifidobacterium animalis* identified as *Bifidobacterium animalis* subsp. *lactis* BIIBS01 and deposited at Deutsche Sammlung von Mikroorganismen und Zellkulturen GmbH (DSMZ) under deposit number DSM 33233,
  a bacterial strain belonging to the species *Lactobacillus plantarum* identified as *Lactobacillus plantarum* LpIBS01 and deposited at Deutsche Sammlung von Mikroorganismen und Zellkulturen GmbH (DSMZ) under deposit number DSM 33234, and
  a mixture thereof; and,
optionally, said composition comprises at least one acceptable pharmaceutical or food grade additive and/or excipient.

FRa 2. The composition for use according to FRa1, wherein said at least one amino acid is selected from the group A comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

FRa 3. The composition for use according to FRas 1 or 2, wherein said mixture M comprises at least one bacterial strain, or a derivative thereof, selected from the group comprising, or alternatively, consisting of:
  *Lactobacillus paracasei* DG® CNCM I-1572,
  *Lactobacillus paracasei* LPC-S01™ DSM 26760,
  and a mixture thereof.

FRa 4. The composition for use according to FRa 3, wherein said mixture M further comprises at least one bacterial strain, or a derivative thereof, selected from the group comprising, or alternatively, consisting of:
  *Bifidobacterium breve* BbIBS01 DSM 33231,
  *Bifidobacterium breve* BbIBS02 DSM 33232,
  *Bifidobacterium animalis* subsp. *lactis* BIIBS01 DSM 33233,
  *Lactobacillus plantarum* LpIBS01 DSM 33234, and
  a mixture thereof.

FRa 5. The composition for use according to any one of FRas 1 to 4, wherein said composition further comprises at least one protein of plant origin, and/or at least one peptide of plant origin, and/or at least one amino acid; preferably wherein said amino acid comprised in the composition is selected from the group A according to FRa 2.

FRa 6. The composition for use according to any one of FRas 1 to 5, wherein said subject suffers from a disease, symptom and/or disorder related with a protein deficiency or with an increased protein requirement. FRa 7. The composition for use according to FRa 6, wherein said disease, symptom and/or disorder related with said protein deficiency or with said increased protein requirement is selected from: decrease in metabolic efficiency, decrease in corpusculated elements in the blood, changes in healing processes, decrease in muscle strength, decrease in muscle mass, muscle depletion, weight loss, decrease in athletic performance, early fatigue, difficulty in concentrating, anxiety, changes in sleep, changes in mood, increased susceptibility to infections, digestive deficiency, changes in blood sugar, increased cholesterol, changes in blood-chemical parameters, malnutrition syndrome, such as for example Kwashiorkor or biafra, osteoporosis, decrease in at least one protein-based component of an organism selected from nails, hair, skin, enzymes, neurotransmitters, hormones and immunoglobulins.

FRa 8. A food product comprising
  proteins of plant origin, and
  the mixture M comprising or, alternatively, consisting of at least one bacterial strain selected from the group comprising or, alternatively, consisting of:
    *Lactobacillus paracasei* DG® CNCM I-1572,
    *Lactobacillus paracasei* LPC-S01™ DSM 26760,
    *Bifidobacterium breve* BbIBS01 DSM 33231,
    *Bifidobacterium breve* BbIBS02 DSM 33232,

*Bifidobacterium animalis* subsp. *lactis* BIIBS01 DSM 33233,

*Lactobacillus plantarum* LpIBS01 DSM 33234, and a mixture thereof.

FRa 9. The food product according to FRa 8, wherein said mixture M comprises at least one bacterial strain, or a derivative thereof, selected from the group comprising, or alternatively, consisting of:

*Lactobacillus paracasei* DG® CNCM I-1572,

*Lactobacillus paracasei* LPC-S01™ DSM 26760, and a mixture thereof;

and, optionally, wherein said mixture M further comprises at least one bacterial strain, or a derivative thereof, selected from the group comprising, or alternatively, consisting of:

*Bifidobacterium breve* BbIBS01 DSM 33231,

*Bifidobacterium breve* BbIBS02 DSM 33232,

*Bifidobacterium animalis* subsp. *lactis* BIIBS01 DSM 33233,

*Lactobacillus plantarum* LpIBS01 DSM 33234, and a mixture thereof.

FRa 10. The food product according to FRas 8 or 9, wherein said at least one bacterial strain is in a form of coated viable bacterial strain or coated probiotic, paraprobriotic or postbiotic; preferably at least one bacterial strain is in a form selected from the group comprising or, alternatively, consisting of: coated viable bacterial strain, tyndallized bacterial strain, sonicated bacterial strain, inactivated bacterial strain, lysate of the bacterial strain, extract of the bacterial strain, a component of the bacterial strain selected from exopolysaccharide, parietal fraction, metabolite and metabolic bioproduct.

FRa 11. The food product according to any one of FRas 8 to 10 for use in increasing the blood bioavailability of at least one amino acid derived from said proteins of plant origin.

Preferred embodiments of the present disclosure FRbn are reported below.

FRb1. A composition for use in increasing the blood bioavailability of at least one amino acid derived from a protein of plant origin in a subject who takes said protein of plant origin or said at least one amino acid or a peptide of plant origin comprising said at least one amino acid through oral route, wherein said composition comprises a mixture M comprising, or alternatively, consisting of at least one bacterial strain, or a derivative thereof, selected from the group comprising, or alternatively, consisting of:

a bacterial strain belonging to the species *Lactobacillus paracasei* identified as *Lactobacillus paracasei* DG® and deposited at the National Collection of Cultures of Microorganisms of the Pasteur Institute in Paris under the accession number CNCM I-1572, a bacterial strain belonging to the species *Lactobacillus paracasei* identified as *Lactobacillus paracasei* LPC-S01™ and deposited at Sammlung von Mikroorganismen und Zellkulturen GmbH (DSMZ) under accession number DSM 26760, a bacterial strain belonging to the species *Bifidobacterium breve* identified as *Bifidobacterium breve* BbIBS01 and deposited at Deutsche Sammlung von Mikroorganismen und Zellkulturen GmbH (DSMZ) under deposit number DSM 33231, a bacterial strain belonging to the species *Bifidobacterium breve* identified as *Bifidobacterium breve* BbIBS02 and deposited at Deutsche Sammlung von Mikroorganismen und Zellkulturen GmbH (DSMZ) under deposit number DSM 33232, a bacterial strain belonging to the species *Bifidobacterium animalis* identified as *Bifidobacterium animalis* subsp. *lactis* BIIBS01 and deposited at Deutsche Sammlung von Mikroorganismen und Zellkulturen GmbH (DSMZ) under deposit number DSM 33233, a bacterial strain belonging to the species *Lactobacillus plantarum* identified as *Lactobacillus plantarum* LpIBS01 and deposited at Deutsche Sammlung von Mikroorganismen und Zellkulturen GmbH (DSMZ) under deposit number DSM 33234, and a mixture thereof; and, optionally, said composition comprises at least one acceptable pharmaceutical or food grade additive and/or excipient, wherein said at least one amino acid is selected from the group A comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

FRb2. The composition for use according to FRb 1, wherein said at least one amino acid is selected from the group A.1.a comprising or, alternatively, consisting of: asparagine, alanine, methionine, aspartic acid, histidine, valine, tryptophan, leucine, phenylalanine, isoleucine, tyrosine and mixtures thereof.

FRb3. The composition for use according to FRb 1 or 2, wherein said mixture M comprises at least one bacterial strain, or a derivative thereof, selected from the group comprising or, alternatively, consisting of:

*Lactobacillus paracasei* DG® CNCM I-1572,

*Lactobacillus paracasei* LPC-S01™ DSM 26760, and a mixture thereof, preferably at a 1:1 by weight ratio.

FRb4. The composition for use according to FRb3, wherein said mixture M further comprises at least one bacterial strain, or a derivative thereof, selected from the group comprising or, alternatively, consisting of:

*Bifidobacterium breve* BbIBS01 DSM 33231,

*Bifidobacterium breve* BbIBS02 DSM 33232,

*Bifidobacterium animalis* subsp. *lactis* BIIBS01 DSM 33233,

*Lactobacillus plantarum* LpIBS01 DSM 33234, and a mixture thereof.

FRb5. The composition for use according to any one of FRbs 1 to 4, wherein said composition further comprises at least one protein of plant origin, and/or at least one peptide of plant origin, and/or at least one amino acid; preferably wherein said amino acid comprised in the composition is selected from the group A according to FRb 2.

FRb6. The composition for use according to any one of FRbs 1 to 5, wherein said subject suffers from disease, symptom and/or disorder associated with a protein deficiency or increased protein requirement. FRb7. The composition for use according to FRb 6, wherein said disease, symptom and/or disorder associated with said protein deficiency or with said increased protein requirement is selected from: decrease in metabolic efficiency, decrease in corpusculated elements in the blood, changes in healing processes, decrease in muscle strength, decrease in muscle mass, muscle depletion, weight loss, decrease in athletic performance, early fatigue, difficulty in concentrating, anxiety, changes in sleep, changes in mood, increased susceptibility to infections, digestive deficiency, changes in blood sugar, increased cholesterol, changes in blood-chemical parameters, malnutrition syndrome such as Kwashorkor or biafra, osteoporosis, reduction of at least one protein-based component of an organism selected from nails, hair, skin, enzymes, neurotransmitters, hormones and immunoglobulins.

FRb8. A food product comprising
proteins of plant origin, and
the mixture M comprising or, alternatively, consisting of
at least one bacterial strain selected from the group comprising or, alternatively, consisting of:
Lactobacillus paracasei DG® CNCM I-1572,
Lactobacillus paracasei LPC-S01™ DSM 26760,
Bifidobacterium breve BbIBS01 DSM 33231,
Bifidobacterium breve BbIBS02 DSM 33232,
Bifidobacterium animalis subsp. lactis BIIBS01 DSM 33233,
Lactobacillus plantarum LpIBS01 DSM 33234, and
a mixture thereof.

FRb9. The food product according to FRb 8, wherein said mixture M comprises at least one bacterial strain, or a derivative thereof, selected from the group comprising or, alternatively, consisting of:
Lactobacillus paracasei DG® CNCM I-1572,
Lactobacillus paracasei LPC-S01™ DSM 26760, and
a mixture thereof;
and, optionally, wherein said mixture M further comprises at least one bacterial strain, or a derivative thereof, selected from the group comprising, or alternatively, consisting of:
Bifidobacterium breve BbIBS01 DSM 33231,
Bifidobacterium breve BbIBS02 DSM 33232,
Bifidobacterium animalis subsp. lactis BIIBS01 DSM 33233,
Lactobacillus plantarum LpIBS01 DSM 33234, and
a mixture thereof.

FRb10. The food product according to FRb 8 or 9, wherein said at least one bacterial strain is in a form of a coated viable bacterial strain or coated paraprobiotic or postbiotic, or probiotic; preferably at least one bacterial strain is in a form selected from the group comprising or, alternatively, consisting of: coated viable bacterial strain, tyndallized bacteria strain, sonicated bacterial strain, inactivated bacteria strain, lysate of the bacterial strain, extract of the bacterial strain, a component of the bacterial strain selected from exopolysaccharide, parietal fraction, metabolite and metabolic bioproduct.

FRb11. The food product according to any of FRbs 8 to 10 for use in increasing the blood bioavailability of at least one amino acid derived from said proteins of plant origin.

FRb12. A non-therapeutic use of a composition for increasing the blood bioavailability of at least one amino acid derived from a protein of plant origin in a subject taking—through oral route—said protein of plant origin or said at least one amino acid or a peptide of plant origin comprising said at least one amino acid, wherein said composition comprises a mixture M comprising, or alternatively, consisting of at least one bacterial strain, or a derivative thereof, selected from the group comprising, or alternatively, consisting of:
a bacterial strain belonging to the species Lactobacillus paracasei identified as Lactobacillus paracasei DG® and deposited at the National Collection of Cultures of Microorganisms of the Pasteur Institute in Paris under the accession number CNCM I-1572,
a bacterial strain belonging to the species Lactobacillus paracasei identified as Lactobacillus paracasei LPC-S01™ and deposited at Sammlung von Mikroorganismen und Zellkulturen GmbH (DSMZ) under accession number DSM 26760,
a bacterial strain belonging to the species Bifidobacterium breve identified as Bifidobacterium breve BbIBS01 and deposited at Deutsche Sammlung von Mikroorganismen und Zellkulturen GmbH (DSMZ) under deposit number DSM 33231,
a bacterial strain belonging to the species Bifidobacterium breve identified as Bifidobacterium breve BbIBS02 and deposited at Deutsche Sammlung von Mikroorganismen und Zellkulturen GmbH (DSMZ) under deposit number DSM 33232,
a bacterial strain belonging to the species Bifidobacterium animalis identified as Bifidobacterium animalis subsp. lactis BIIBS01 and deposited at Deutsche Sammlung von Mikroorganismen und Zellkulturen GmbH (DSMZ) under deposit number DSM 33233,
a bacterial strain belonging to the species Lactobacillus plantarum identified as Lactobacillus plantarum LpIBS01 and deposited at Deutsche Sammlung von Mikroorganismen und Zellkulturen GmbH (DSMZ) under deposit number DSM 33234, and
a mixture thereof; and,
optionally, said composition comprises at least one acceptable pharmaceutical or food grade additive and/or excipient, wherein said at least one amino acid is selected from the group A comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

FRb13. A method for increasing the blood bioavailability of at least one amino acid derived from a protein of plant origin in a subject taking—through oral route—said protein of plant origin or said at least one amino acid or a peptide of plant origin comprising said at least one amino acid, wherein said method comprises administering a composition comprising a mixture M comprising or, alternatively, consisting of at least one bacterial strain or a derivative thereof, selected from the group comprising or, alternatively, consisting of:
a bacterial strain belonging to the species Lactobacillus paracasei identified as Lactobacillus paracasei DG® and deposited at the National Collection of Cultures of Microorganisms of the Pasteur Institute in Paris under the accession number CNCM I-1572,
a bacterial strain belonging to the species Lactobacillus paracasei identified as Lactobacillus paracasei LPC-S01™ and deposited at Sammlung von Mikroorganismen und Zellkulturen GmbH (DSMZ) under accession number DSM 26760,
a bacterial strain belonging to the species Bifidobacterium breve identified as Bifidobacterium breve BbIBS01 and deposited at Deutsche Sammlung von Mikroorganismen und Zellkulturen GmbH (DSMZ) under deposit number DSM 33231,
a bacterial strain belonging to the species Bifidobacterium breve identified as Bifidobacterium breve BbIBS02 and deposited at Deutsche Sammlung von Mikroorganismen und Zellkulturen GmbH (DSMZ) under deposit number DSM 33232,
a bacterial strain belonging to the species Bifidobacterium animalis identified as Bifidobacterium animalis subsp. lactis BIIBS01 and deposited at Deutsche Sammlung von Mikroorganismen und Zellkulturen GmbH (DSMZ) under deposit number DSM 33233,
a bacterial strain belonging to the species Lactobacillus plantarum identified as Lactobacillus plantarum LpIBS01 and deposited at Deutsche Sammlung von Mikroorganismen und Zellkulturen GmbH (DSMZ) under deposit number DSM 33234, and a mixture thereof; and, optionally, said composition comprises at least one acceptable pharmaceutical or food grade additive and/or excipient, and wherein, said at least one amino acid is selected from the group A comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

FRb14. A probiotic bacterial strain (I.i) *Lactobacillus paracasei* DG® CNCM I-1572 (freeze-dried in powder form), for use in increasing the blood bioavailability of at least one amino acid derived from a protein of plant or animal origin, preferably from a protein of plant origin, in a subject taking—through oral route—said protein or at least one amino acid or a peptide of plant origin comprising said at least one amino acid.

FRb15. A probiotic bacterial strain (I.ii) *Lactobacillus paracasei* LPC-S01™ DSM 26760 (freeze-dried in powder form), for use in increasing the blood bioavailability of at least one amino acid derived from a protein of plant or animal origin, preferably from a protein of plant origin, in a subject taking—through oral route—said protein or at least one amino acid or a peptide of plant origin comprising said at least one amino acid.

Further details concerning the compositions methods and systems of the present disclosure, can be identified by the person skilled in the art upon reading of the present disclosure.

EXAMPLES

The, bacteria, compositions, food products and related methods and system herein disclosed are further illustrated in the following examples, which are provided by way of illustration and are not intended to be limiting. In particular, exemplary LP-DG® (CNCM I-1572), and *L. paracasei* LPC-S01™ (DSM 26760) and related compositions methods and systems are described in connection with an In vitro test and a clinical trial in humans. A skilled person will be able to understand and identify the modifications required to adapt the results illustrated in the exemplary embodiments of this sections to additional embodiments of the compositions, food products, methods and systems in accordance with the present disclosure. Example 1:

In Vitro Test

This trial investigated the effect of the individual strains of LP-DG® (CNCM I-1572), and *L. paracasei* LPC-S01 (DSM 26760) on the in vitro digestion of amino acids derived from different sources of plant proteins, as well as their synergistic effect when taken in combination.

Suspensions of pea or rice protein isolates were incubated with probiotic bacterial strains (LP-DG® (CNCM I-1572) and/or *L. paracasei* LPC-S01™ (DSM 26760)) in the presence and in the absence of porcine pepsin (EC 3.4.23.1; Sigma-Aldrich, Milan, Italy) and pancreatin (Sigma-Aldrich, Milan, Italy).

In particular, 0.8 mL of the pea and/or rice protein isolate suspension (10 g/L) was mixed with 0.02 mL of porcine gastric pepsin solution (2 g/L in water). After 1 hour of incubation at 37° C. under mixing, the pH was adjusted to ≈8.0 by adding 1 M Tris base and 0.2 mL of porcine pancreas pancreatin (2 g/L in 0.1 M Tris-HCl Buffer, pH 7.5; CE 232-468-9).

Pancreatin digestion was carried out for 3 hours in the absence or in the presence of 0.1 mL of probiotic cells ((LP-DG® (CNCM I-1572), and/or *L. paracasei* LPC-S01™ (DSM 26760)) (250 g/L in 0.1 M Tris-HCl buffer, pH 7.5).

The peptides released by proteolysis under all the conditions tested were evaluated by adding trichloroacetic acid (TCA) to an aliquot of each reaction mixture (suspension of proteins+pepsin and pancreatin with and without the probiotic strains mentioned above) up to obtaining a final amount of 10% (by volume). After centrifuging at 10000×g for 25 min at room temperature, the absorbance of the supernatant from which the amount of peptides was obtained was measured at 280 nm.

As concerns SDS-PAGE analysis, aliquots of the different reaction mixtures were diluted at various incubation times (1/1, v/v dilution) with Laemmli denaturing buffer (0.125 M Tris-HCl, pH 6.8; 50% glycerol; 1.7% SDS; bromophenol blue at 0.01%; 1% 2-mercaptoethanol) and heated at 100° C. for 10 min. SDS-PAGE was conducted on a 12% monomer gel, using a MiniProtein apparatus (Bio-Rad, Richmond, Va., USA) and the gels were stained with Coomassie Blue (triphenylmethane blue dye). SDS page (sodium dodecyl sulfate polyacrylamide gel electrophoresis) is an analytical technique used to separate proteins based on their molecular weight. When the proteins are separated by electrophoresis through a gel matrix. In SDS-PAGE, the use of sodium dodecyl sulfate (SDS, also known as sodium lauryl sulfate) and polyacrylamide gel largely eliminates the influence of structure and charge and proteins are separated solely based on the length of the polypeptide chain.

Aliquots of the various reaction mixtures were treated with 0.1% trifluoroacetic acid (TFA) and subsequently centrifuged at 12000×g for 20 min. (0.1% trifluoroacetic acid (TFA) (by volume). An aliquot of 0.2 mL of reaction mixture was loaded onto a "Symmetry" C18 (300 Å; 3.5 µm; 2.1 mm×50 mm; Waters, Milan, IT) column, previously equilibrated with 0.1% TFA in distilled water and eluted at a flow rate of 0.8 mL/min, with a linear gradient starting from 5 min after injection up to 60% (v/v) of acetonitrile, in the presence of TFA at 0.1% (by volume). The chromatographic separation was carried out with a Waters™ 626 equipment provided with a Waters™ 2487 dual wavelength detector (Waters, Milan, Italy). Data at 220 nm and 280 nm were recorded and processed using Empower Pro software (Waters, Milan, Italy). The results are expressed as the total area of the peak measured at 220 nm including peptides containing no aromatic residues which were quantified by measuring the absorbance—at 280 nm—of the supernatant after treatment with TFA.

Results

RP-HPLC analysis showed in particular that *L. paracasei* LP-DG® showed a particular proteolytic activity for rice protein isolates. In addition, the combination of two strains (LP-DG® (CNCM I-1572) and *L. paracasei* LPC-S01™ (DSM 26760)) showed a synergistic effect, particularly toward pea proteins (Table 5)

Example 2: Clinical Trial in Humans

The purpose of the clinical trial reported below is to examine the effect of ingesting a probiotic combined with a protein (of plant and animal origin) on the subsequent appearance of amino acids in the blood.

Trial Design:

two separate, randomised, double-blind, placebo-controlled crossover designs.

Twenty (n=20) male subjects were randomly assigned to ingest a supplement containing a protein (of plant origin (20 g of pea protein), n=10+5 (see below); or of animal origin, n=10) and a placebo, or a protein (of plant origin (20 g of pea protein), n=10; or of animal origin, n=10) plus a composition according to the disclosure (5 billion CFU L. paracasei LP-DG® (CNCM I-1572) plus 5 billion CFU L. paracasei LPC-S01™ (DSM 26760), SOFAR S.p.A., Italy)) (in short, probiotic) for two weeks prior to the experimental test. The daily diet was recorded and the subjects were requested to repeat the diet for the two weeks leading to the second experimental test.

On the day of the experimental tests, subjects were placed under fasting for at least 12 hours. Subjects were catheterised with a teflon catheter in an antecubital vein for multiple blood draws. The catheter is washed with 2-3 ml of 0.9% sodium chloride. Following basic sampling, the subjects were administered with their respective supplement (ingestion of supplement). Subsequently, blood samples were taken at 30, 60, 120 and 180 minutes after ingestion. Subsequently, a four-week wash-out period was implemented, followed by the opposite condition. The expression opposite condition is used to indicate that a subject taking proteins and placebo in the first cycle will take proteins and probiotics in the second round. FIG. 1 provides a detailed diagram of the trial. Blood was collected and transferred into 8.5 ml Becton Dickinson (BD) test tubes (BD Vacutainer SST) to obtain serum, and into 10.0 ml BD tubes (Vacutainer Sodium Heparin) to obtain plasma and subsequently centrifuged at 1500×g for 15 min at 4° C. The resulting serum and plasma were then split into aliquots and stored at −80° C. until subsequent tests.

Subject Population:

Twenty (n=20) normal weight (body mass index (BMI), 19-24.99 kg×m$^2$) male subjects active at recreational level (according to the American College of Sports Medicine guidelines), normal weight (body mass index (BMI), 19-24.99 kg×m$^2$), aged 20 to 35 years.

The twenty subjects were randomly assigned to the plant protein group (n=10) or animal protein group (n=10). Other 5 subjects were added to the group of 10 subjects assigned to the plant protein group for a total of 15 subjects on whom the statistical analysis reported in the present context is based.

The narrow age group (20-35 years) was chosen as changes in gut microbiota and potentially digestive enzymes could occur over time with age. This ensures consistency among subjects. The subject will not have taken any known nutritional or ergogenic supplements known to be capable of affecting the current trial measures for the previous 6 weeks, nor will they have any medical condition or allergy capable of affecting the outcome of interest.

Material: proteins of plant origin: protein isolated from yellow pea Nutralys® S85F Roquette Freres S.A., France (*Pisum Sativum*), in powder form, loss on drying 10% max, protein content on dry base 84% min Analysis of the amino acid profile of the protein supplement is reported in table 1c below

| Amino acid | mg/g protein |
| --- | --- |
| alanine | 43 |
| arginine | 88 |
| Aspartic acid | 117 |
| cysteine | 9 |
| Glutamic acid | 167 |

-continued

| Amino acid | mg/g protein |
| --- | --- |
| glycine | 41 |
| histidine | 25 |
| isoleucine | 48 |
| leucine | 83 |
| lysine | 74 |
| methionine | 12 |
| phenylalanine | 54 |
| proline | 45 |
| serine | 50 |
| threonine | 40 |
| tryptophan | 10 |
| tyrosine | 39 |
| valine | 51 | probiotic (composition according to the disclosure, AminoAlta ™): mixture of (I.i) *Lactobacillus paracasei* DG ® CNCM I-1572 5 billion CFU (freeze-dried in powder form), (I.ii) *Lactobacillus paracasei* LPC-S01 ™ DSM 26760 billion CFU (freeze-dried in powder form) and, optionally maltodextrin, according to Table 1a and Table 1b.
Placebo: Maltodextrin (Glucidex ® 12, Roquette Freres S.A., France)

The materials to be administered, listed above, were supplied in a sealed sachet separated from each other until the time of consumption. Subjects were instructed to open the sachets and mix the content (protein and placebo, or protein with probiotic) with their favourite non-protein beverage (473 ml).

TABLE 1a

| Ingredients list | Amt per 100 g | Amt per unit |
| --- | --- | --- |
| Maltodextrin | 92.500 g | 1850.000 mg |
| *Lactobacillus Paracasei* LPC-S01 ™ DSM 26760 | 3.750 g | 75.000 mg |
| *Lactobacillus Paracasei* DG ® CNCM I-1572 | 3.750 g | 75.000 mg |
| Total | 100.000 g | 2000.000 mg |

TABLE 1b

| NUTRIENT SUPPLY | | |
| --- | --- | --- |
| Average content | per 100 g | Per daily dose |
| Total count of ferments | 1500.000 bln. C.F.U.* | 30.000 bln. C.F.U.* |
| of which *Lactobacillus Paracasei* LPC-S01 ™ | 750.000 bln. C.F.U* | 15.000 bln. C.F.U.* |
| of which *Lactobacillus Paracasei* DG ® CNCM I-1572 | 750.000 bln. C.F.U.* | 15.000 bln. C.F.U.* |

*Amount of ferments present in formula

Amino Acid Analysis

EZfaast® amino acid analysis kits (Phenomenex, Torrance, Calif.) (U.S. Pat. No. 6,770,246) were used for liquid chromatographic analysis of amino acids using tandem mass spectrometry (LC/MS/MS) and electrospray ionization (ESI). The procedure consists of solid phase extractions of 25 µl plasma with internal standards with an absorbent tip attached to a syringe with an elution solvent (a 3:2 mixture of sodium hydroxide with 77% n-propanol and 23% 3-picoline). The free amino acids were then derivatized by adding a mixture of 17.4% propyl chloroformate, 11% isooctane and 71.6% chloroform (by volume). The resulting mixture was vortexed and allowed to stand at room temperature for 1 minute, followed by liquid-liquid extraction with isooctane. Fifty microliters of the organic layer were removed, dried under nitrogen flow and suspended in the HPLC run solvents before being injected into the LC/MS/

MS. Chromatographic separation of the derivatized amino acids was carried out on an amino acid analysis-mass spectrometry column (250×2.0 mm d.i., 4 μm) using a triple quadrupole Agilent 6460 LC/MS/MS system (Santa Clara, Calif.). Ten millimetres of ammonium formate in water with 0.2% formic acid (by volume) (mobile phase A) and 10 mm of ammonium formate in methanol with 0.2% formic acid (by volume) (mobile phase B) were used as solvent with a gradient from 68% B at 0 min to 83% B over 13 min with a flow rate of 0.25 ml/min. Amino acids and internal standard data were collected using the dynamic multiple reaction monitoring mode using MassHunter acquisition software (Agilent, Santa Clara, Calif.). MassHunter quantification software was used quantify plasma samples based on standard curves.

Result Variables:
amount of amino acids (i.e. 3-methylhistidine, arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine and tyrosine) in peripheral blood measured by means of:
maximum concentration (Cmax);
the corresponding time (Tmax) and area under the curve (AUC), calculated as appropriate.

For statistical analysis, the area under the curve (concentration vs. time, in short AUC) was calculated for each of the 22 amino acids, as well as BCAAs, essential amino acids (EAAs) and total amino acids, through the linear trapezoidal rule and using all available time points. Cmax was defined as the highest observed concentration and Tmax was the time when Cmax was reached. AUC values were compared between conditions through t-test for paired samples. A p value<0.05 was considered statistically significant.

Statistical Analysis:
two separate analyses of two-way repeated measures (subjects administered with proteins of plant origin and with proteins of animal origin) of variance are used to determine differences in result variables. Significance was set to an alpha level of 0.05. When a significant major effect and/or interaction was observed, a post-hoc analysis was performed using Bonferronni correction. Furthermore, magnitude-based inference was used.

Contrary to the null-based hypothesis test (p-value), magnitude-based inference allows an analysis of the response based on clinical significance.

Results:
Tables (2), (3) and (4) report the results of the statistical analysis of the subjects (n=10) participating in the clinical trial administered with protein of plant origin, or with protein of plant origin plus probiotic (composition according to the disclosure).

In particular,
Table 2 reports the total concentration data (AUC, area under the curve) for the amino acids analysed;
Table 3 reports the Cmax (maximum concentration) data for the amino acids analysed;
Table 4 reports the data of Tmax (in minutes) (time at which the maximum concentration is recorded) for the amino acids analysed.

The statistical analysis revealed—in subjects who took plant proteins plus probiotic—both a higher maximum concentration (Cmax) and a higher total concentration (AUC) for methionine, histidine, valine, leucine, isoleucine, tyrosine, total BCAAs and total EAAs.

In particular, the administration of the composition of the disclosure comprising the aforementioned bacterial strains (AminoAlta™) resulted in a statistically significant increase in AUC and Cmax for methionine (AUC: +20%, p=0.007; Cmax: +16.3%, p=0.008), histidine (AUC:+40.4%, p=0.009; Cmax: +49.2%, p=0.048), valine (AUC:+21.5%, p=0.013; Cmax: +24.7%, p=0.034), leucine (AUC:+23.3%, p=0.006; Cmax: +25.2%, p=0.043), isoleucine (AUC:+26.0%, p=0.017; Cmax: +26.1%, p=0.020), tyrosine (AUC:+16.0%, p=0.009; Cmax: +11.6, p=0.014), total BCAAs (AUC:+22.8%, p=0.008; Cmax: +26.8, p=0.009) and total EAAs (AUC:+16.0%, p=0.005; Cmax: +15.6, p=0.022) without significantly modifying the time to reach maximum concentrations.

Furthermore, no significant changes were observed between the Tmax of subjects administered with plant protein and the Tmax of subjects administered with the plant protein plus probiotic.

CONCLUSIONS

Thus, the administration of the composition according to the disclosure (AminoAlta™) can be an important nutritional strategy to improve protein utilisation and overcome the compositional deficiencies of plant proteins.

TABLE 2

| | AUC | | | | Protein + Probiotic vs Protein | |
|---|---|---|---|---|---|---|
| | Protein + Probiotic | | Protein | | % | Effect |
| | Mean value | SD | Mean value | SD | p-value (t-test) | Difference | Size (d) |
| Arginine | 14490.3 | 4677.7 | 13954.3 | 6498.0 | 0.585 | 3.8 | 0.10 |
| Glutamine | 90876.4 | 21491.3 | 87569.0 | 25645.0 | 0.649 | 3.8 | 0.14 |
| Citrulline | 3936.4 | 1411.6 | 5922.3 | 1906.1 | 0.967 | 0.4 | 0.01 |
| Serine | 17569.1 | 4194.0 | 17464.6 | 6513.0 | 0.942 | 0.6 | 0.02 |
| Asparagine | 13305.5 | 3226.3 | 12212.4 | 3774.1 | 0.337 | 9.0 | 0.31 |
| Glycine | 33083.9 | 9728.7 | 32626.4 | 10309.8 | 0.874 | 1.4 | 0.05 |
| Threonine | 22917.0 | 4289.4 | 21905.7 | 6917.8 | 0.621 | 4.6 | 0.18 |
| Alanine | 56904.7 | 13342.8 | 53750.8 | 20418.2 | 0.496 | 5.9 | 0.18 |
| Ornithine | 10060.4 | 3354.2 | 9793.9 | 3678.8 | 0.693 | 2.7 | 0.08 |
| Methionine | 3558.9 | 1462.0 | 2966.9 | 1245.0 | 0.007 | 20.0 | 0.44 |
| Proline | 43142.9 | 10833.0 | 42124.2 | 19636.2 | 0.780 | 2.4 | 0.06 |
| Lysine | 36177.2 | 5057.1 | 35387.7 | 10758.1 | 0.759 | 2.2 | 0.09 |

TABLE 2-continued

| | AUC | | | | | | |
|---|---|---|---|---|---|---|---|
| | Protein + Probiotic | | Protein | | Protein + Probiotic vs Protein | | |
| | Mean value | SD | Mean value | SD | p-value (t-test) | % Difference | Effect Size (d) |
| Aspartic ac. | 711.7 | 259.4 | 591.5 | 277.9 | 0.125 | 20.4 | 0.45 |
| Histidine | 14388.0 | 4519.9 | 10248.1 | 3983.4 | 0.009 | 40.4 | 0.97 |
| Valine | 65216.4 | 17782.9 | 53682.1 | 17525.3 | 0.013 | 21.5 | 0.65 |
| Glutamic ac. | 6523.0 | 3703.0 | 6384.9 | 3079.4 | 0.849 | 2.2 | 0.04 |
| Tryptophan | 13056.3 | 4319.6 | 12078.2 | 3535.2 | 0.276 | 8.1 | 0.25 |
| Leucine | 26443.5 | 10874.2 | 21447.6 | 10701.1 | 0.006 | 23.3 | 0.46 |
| Phenylalanine | 8879.6 | 2629.0 | 8061.8 | 3371.5 | 0.086 | 10.1 | 0.27 |
| Isoleucine | 19048.2 | 6642.5 | 15116.5 | 5961.5 | 0.017 | 26.0 | 0.62 |
| Cysteine | 3016.2 | 932.8 | 3024.9 | 1458.0 | 0.978 | −0.3 | −0.01 |
| Tyrosine | 10790.8 | 3532.4 | 9306.0 | 3923.5 | 0.009 | 16.0 | 0.40 |
| Total BCAAs | 110836.8 | 33142.0 | 90304.5 | 33001.5 | 0.008 | 22.8 | 0.62 |
| Total EAAs | 210115.0 | 41010.5 | 181071.7 | 54739.9 | 0.005 | 16.0 | 0.60 |
| Total AAs | 515152.2 | 79378.2 | 474059.9 | 139979.5 | 0.136 | 8.7 | 0.36 |

TABLE 3

| | Cmax | | | | | | |
|---|---|---|---|---|---|---|---|
| | Protein + Probiotic | | Protein | | Protein + Probiotic vs Protein | | |
| | Mean value | SD | Mean value | SD | p-value (t-test) | % Difference | Effect (d) |
| Arginine | 102.4 | 30.9 | 106.6 | 42.9 | 0.556 | −3.9 | −0.11 |
| Glutamine | 601.7 | 131.8 | 599.9 | 131.2 | 0.974 | 0.3 | 0.01 |
| Citrulline | 26.4 | 9.7 | 27.4 | 10.5 | 0.580 | −3.6 | −0.10 |
| Serine | 128.3 | 28.4 | 130.4 | 47.5 | 0.860 | −1.6 | −0.05 |
| Asparagine | 101.3 | 22.6 | 96.1 | 31.0 | 0.602 | 5.5 | 0.19 |
| Glycine | 228.3 | 56.7 | 237.3 | 66.5 | 0.625 | −3.8 | −0.15 |
| Threonine | 161.9 | 30.5 | 159.2 | 51.0 | 0.861 | 1.7 | 0.06 |
| Alanine | 414.6 | 148.2 | 389.6 | 135.3 | 0.418 | 6.4 | 0.18 |
| Ornithine | 72.8 | 23.4 | 72.0 | 23.7 | 0.881 | 1.2 | 0.04 |
| Methionine | 23.2 | 8.9 | 19.9 | 6.3 | 0.008 | 16.3 | 0.42 |
| Proline | 318.7 | 129.1 | 323.0 | 176.2 | 0.905 | −1.3 | −0.03 |
| Lysine | 276.0 | 45.9 | 266.0 | 70.5 | 0.627 | 3.7 | 0.17 |
| Aspartic ac. | 7.3 | 3.6 | 5.9 | 3.6 | 0.208 | 22.7 | 0.37 |
| Histidine | 110.0 | 59.1 | 73.7 | 24.5 | 0.048 | 49.2 | 0.80 |
| Valine | 490.5 | 174.5 | 393.4 | 94.2 | 0.034 | 24.7 | 0.69 |
| Glutamic ac. | 50.4 | 24.3 | 51.9 | 22.5 | 0.740 | −3.0 | −0.07 |
| Tryptophan | 90.8 | 24.7 | 88.7 | 19.7 | 0.796 | 2.4 | 0.10 |
| Leucine | 200.7 | 80.3 | 160.3 | 71.6 | 0.043 | 25.2 | 0.53 |
| Phenylalanine | 57.6 | 16.8 | 54.8 | 18.9 | 0.252 | 5.2 | 0.16 |
| Isoleucine | 149.4 | 46.8 | 118.4 | 41.6 | 0.020 | 26.1 | 0.70 |
| Cysteine | 19.5 | 5.3 | 19.8 | 7.5 | 0.832 | −1.8 | −0.06 |
| Tyrosine | 70.6 | 23.2 | 63.3 | 22.6 | 0.014 | 11.6 | 0.32 |
| Total BCAAs | 833.8 | 237.5 | 657.8 | 192.6 | 0.009 | 26.8 | 0.81 |
| Total EAAs | 1512.6 | 315.7 | 1308.2 | 301.3 | 0.022 | 15.6 | 0.66 |
| Total AAs | 3566.6 | 586.2 | 3389.4 | 818.6 | 0.371 | 5.2 | 0.25 |

TABLE 4

| | Tmax | | | | | | |
|---|---|---|---|---|---|---|---|
| | Protein + Probiotic | | Protein | | Protein + Probiotic vs Protein | | |
| | Mean value | SD | Mean value | SD | p-value (t-test) | % Difference | Effect (d) |
| Arginine | 58.0 | 41.6 | 40.0 | 14.6 | 0.057 | 45.0 | 0.58 |
| Glutamine | 54.0 | 41.2 | 60.0 | 56.7 | 0.748 | −10.0 | −0.12 |
| Citrulline | 56.0 | 46.6 | 48.0 | 49.2 | 0.546 | 16.7 | 0.17 |
| Serine | 52.0 | 40.0 | 40.0 | 29.3 | 0.271 | 30.0 | 0.34 |
| Asparagine | 58.0 | 43.1 | 46.0 | 33.8 | 0.395 | 26.1 | 0.31 |
| Glycine | 70.0 | 55.2 | 52.0 | 56.1 | 0.398 | 34.6 | 0.32 |
| Threonine | 52.0 | 51.3 | 50.0 | 40.4 | 0.458 | 24.0 | 0.26 |
| Alanine | 78.0 | 54.1 | 56.0 | 49.3 | 0.294 | 39.3 | 0.43 |
| Ornithine | 72.0 | 45.1 | 52.0 | 33.0 | 0.096 | 38.5 | 0.51 |
| Methionine | 48.0 | 42.1 | 38.0 | 13.7 | 0.388 | 26.3 | 0.32 |
| Proline | 66.0 | 53.4 | 56.0 | 54.2 | 0.632 | 17.9 | 0.19 |
| Lysine | 50.0 | 40.4 | 54.0 | 44.2 | 0.784 | −7.4 | −0.09 |
| Aspartic ac. | 46.0 | 35.6 | 50.0 | 43.4 | 0.774 | −8.0 | −0.10 |
| Histidine | 52.0 | 51.3 | 44.0 | 43.7 | 0.246 | 40.9 | 0.38 |
| Valine | 60.0 | 40.9 | 58.0 | 53.7 | 0.914 | 3.4 | 0.04 |
| Glutamic ac. | 42.0 | 37.3 | 74.0 | 69.8 | 0.088 | −43.2 | −0.57 |
| Tryptophan | 52.0 | 43.1 | 72.0 | 54.1 | 0.191 | −27.8 | −0.41 |
| Leucine | 60.0 | 40.9 | 44.0 | 15.5 | 0.120 | 36.4 | 0.52 |
| Phenylalanine | 52.0 | 24.0 | 42.0 | 15.2 | 0.096 | 23.8 | 0.50 |
| Isoleucine | 52.0 | 38.4 | 44.0 | 15.5 | 0.413 | 18.2 | 0.27 |
| Cysteine | 54.0 | 45.6 | 72.0 | 58.7 | 0.447 | −25.0 | −0.34 |
| Tyrosine | 58.0 | 36.7 | 46.0 | 15.5 | 0.233 | 26.1 | 0.43 |
| Total BCAAs | 55.5 | 42.7 | 54.0 | 39.6 | 0.458 | 22.2 | 0.29 |
| Total EAAs | 50.0 | 40.9 | 54.0 | 39.6 | 0.689 | 11.1 | 0.15 |
| Total AAs | 58.0 | 43.1 | 60.0 | 52.0 | 0.910 | −3.3 | −0.04 |

TABLE 5

| | Rice | | Pea | |
|---|---|---|---|---|
| Treatment | Area (*10⁶) | Δ, % | Area (*10⁶) | Δ, % |
| Absorbance at 220 nm | | | | |
| Pepsin + pancreatin | 78.2 ± 0.10 | | 107 ± 0.60 | |
| Pepsin + pancreatin + L. paracasei LP-DG | 80.2 ± 0.15* | +2.6 | 107 ± 0.50 | 0 |
| Pepsin + pancreatin + L. paracasei LPC-S01 | 78.4 ± 0.21 | +0.3 | 111 ± 0.80* | +3.7 |

TABLE 5-continued

|  | Rice | | Pea | |
|---|---|---|---|---|
| Treatment | Area (*$10^6$) | Δ, % | Area (*$10^6$) | Δ, % |
| Pepsin + pancreatin + LP-DG + LPC-S01 Absorbance at 280 nm | 80.6 ± 0.18* | +3.1 | 114 ± 0.70** | +6.5 |
| Pepsin + pancreatin | 5.1 ± 0.10 |  | 11.9 ± 0.06 |  |
| Pepsin + pancreatin + L. paracasei LP-DG | 5.4 ± 0.09* | +5.9 | 12.0 ± 0.08 | +0.8 |
| Pepsin + pancreatin + L. paracasei LPC-S01 | 5.2 ± 0.08 | +2.0 | 12.2 ± 0.02* | +2.5 |
| Pepsin + pancreatin + LP-DG + LPC-S01 | 5.4 ± 0.10* | +5.9 | 12.6 ± 0.07** | +5.6 |

The data are presented as means ± standard deviation
*significantly different from control ($p < 0.05$)
**significantly different from control and individual strain ($p < 0.05$)

In summary described herein are compositions and related food products methods and systems for use in increasing blood bioavailability of amino acids derived from proteins, preferably proteins of plant origin, wherein said compositions comprise a mixture M comprising or, alternatively, consisting of at least one bacterial strain, preferably *Lactobacillus paracasei* DG® CNCM I-1572 and/or *Lactobacillus paracasei* LPC-S01™ DSM 26760, and possibly further comprising at least one protein, preferably proteins of plant origin, or a peptide or an amino acid. In particular, described herein is a food product comprising proteins, preferably of plant origin, and said mixture M of at least one bacterial strain. According to a first set of embodiments a composition and related food products methods and systems are described for use in increasing the blood bioavailability of at least one amino acid derived from a protein of plant origin in a subject who takes said protein of plant origin or said at least one amino acid or a peptide of plant origin comprising said at least one amino acid through oral route.

In the composition and related food products methods and systems of the first set of embodiments said composition comprises a mixture M comprising, or alternatively, consisting of at least one bacterial strain, or a derivative thereof, selected from the group comprising, or alternatively, consisting of:
    a bacterial strain belonging to the species *Lactobacillus paracasei* identified as *Lactobacillus paracasei* DG® and deposited at the National Collection of Cultures of Microorganisms of the Pasteur Institute in Paris under the accession number CNCM I-1572,
    a bacterial strain belonging to the species *Lactobacillus paracasei* identified as *Lactobacillus paracasei* LPC-S01™ and deposited at Sammlung von Mikroorganismen and Zellkulturen GmbH (DSMZ) under accession number DSM 26760,
    a bacterial strain belonging to the species *Bifidobacterium breve* identified as *Bifidobacterium breve* BbIBS01 and deposited at Deutsche Sammlung von Mikroorganismen und Zellkulturen GmbH (DSMZ) under deposit number DSM 33231,
    a bacterial strain belonging to the species *Bifidobacterium breve* identified as *Bifidobacterium breve* BbIBS02 and deposited at Deutsche Sammlung von Mikroorganismen und Zellkulturen GmbH (DSMZ) under deposit number DSM 33232,
    a bacterial strain belonging to the species *Bifidobacterium animalis* identified as *Bifidobacterium animalis* subsp. *lactis* BIIBS01 and deposited at Deutsche Sammlung von Mikroorganismen und Zellkulturen GmbH (DSMZ) under deposit number DSM 33233,
    a bacterial strain belonging to the species *Lactobacillus plantarum* identified as *Lactobacillus plantarum* LpIBS01 and deposited at Deutsche Sammlung von Mikroorganismen und Zellkulturen GmbH (DSMZ) under deposit number DSM 33234, and
    a mixture thereof.

The composition and related food products methods and systems of the first set of embodiments optionally, comprises at least one acceptable pharmaceutical or food grade additive and/or excipient, wherein said at least one amino acid is selected from the group A comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

In any one of the embodiments of the first set of embodiments the in the composition and related food products methods and systems said at least one amino acid can be selected from the group A.1.a comprising or, alternatively, consisting of: asparagine, alanine, methionine, aspartic acid, histidine, valine, tryptophan, leucine, phenylalanine, isoleucine, tyrosine and mixtures thereof.

In any one of the embodiments of the first set of embodiments the in the composition and related food products methods and systems, said mixture M can comprise at least one bacterial strain, or a derivative thereof, selected from the group comprising, or alternatively, consisting of:
    *Lactobacillus paracasei* DG® CNCM I-1572,
    *Lactobacillus paracasei* LPC-S01™ DSM 26760,
and a mixture thereof, preferably at a 1:1 by weight ratio.

In any one of the embodiments of the first set of embodiments the in the composition and related food products methods and systems, said mixture M can comprise or further comprises at least one bacterial strain, or a derivative thereof, selected from the group comprising, or alternatively, consisting of:
    *Bifidobacterium breve* BbIBS01 DSM 33231,
    *Bifidobacterium breve* BbIBS02 DSM 33232,
    *Bifidobacterium animalis* subsp. *lactis* BIIBS01 DSM 33233,
    *Lactobacillus plantarum* LpIBS01 DSM 33234, and
    a mixture thereof.

In any one of the embodiments of the first set of embodiments the in the composition and related food products methods and systems, said composition can further comprises at least one protein of plant origin, and/or at least one peptide of plant origin, and/or at least one amino acid; preferably wherein said amino acid comprised in the composition can be selected from the group A or A1a In any one of the embodiments of the first set of embodiments the in the composition and related food products methods and systems, said subject possibly suffers from a disease, symptom and/or disorder related with a protein deficiency or with an increased protein requirement.

In any one of the embodiments of the first set of embodiments the in the composition and related food products methods and systems said disease, symptom and/or disorder can be related with said protein deficiency or with said increased protein requirement is selected from: decrease in metabolic efficiency, decrease in corpusculated elements in the blood, changes in healing processes, decrease in muscle strength, decrease in muscle mass, muscle depletion, weight loss, decrease in athletic performance, early fatigue, difficulty in concentrating, anxiety, changes in sleep, changes in mood, increased susceptibility to infections, digestive deficiency, changes in blood sugar, increased cholesterol, changes in blood-chemical parameters, malnutrition syndrome, such as for example Kwashiorkor or biafra, osteoporosis, decrease in at least one protein-based component of an organism selected from nails, hair, skin, enzymes, neurotransmitters, hormones and immunoglobulins.

According to a second set of embodiments, a food product is described and related compositions methods and systems, comprising
proteins of plant origin, and
the mixture M comprising or, alternatively, consisting of at least one bacterial strain selected from the group comprising or, alternatively, consisting of:
Lactobacillus paracasei DG® CNCM I-1572,
Lactobacillus paracasei LPC-S01™ DSM 26760,
Bifidobacterium breve BbIBS01 DSM 33231,
Bifidobacterium breve BbIBS02 DSM 33232,
Bifidobacterium animalis subsp. lactis BlIBS01 DSM 33233,
Lactobacillus plantarum LpIBS01 DSM 33234, and
a mixture thereof.

In any one of the embodiments of the second set of embodiments in the food product and related compositions, methods and systems, said mixture M can comprise at least one bacterial strain, or a derivative thereof, selected from the group comprising, or alternatively, consisting of:
Lactobacillus paracasei DG® CNCM I-1572,
Lactobacillus paracasei LPC-S01™ DSM 26760, and
a mixture thereof;

In any one of the embodiments of the second set of embodiments in the food product and related compositions, methods and systems, said mixture M, can comprise or further comprise at least one bacterial strain, or a derivative thereof, selected from the group comprising, or alternatively, consisting of:
Bifidobacterium breve BbIBS01 DSM 33231,
Bifidobacterium breve BbIBS02 DSM 33232,
Bifidobacterium animalis subsp. lactis BlIBS01 DSM 33233,
Lactobacillus plantarum LpIBS01 DSM 33234, and
a mixture thereof.

In any one of the embodiments of the second set of embodiments in the food product and related compositions, methods and systems, said at least one bacterial strain is in a form of coated viable bacterial strain or coated probiotic, paraprobiotic or postbiotic; preferably at least one bacterial strain is in a form selected from the group comprising or, alternatively, consisting of: coated viable bacterial strain, tyndallized bacterial strain, sonicated bacterial strain, inactivated bacterial strain, lysate of the bacterial strain, extract of the bacterial strain, a component of the bacterial strain selected from exopolysaccharide, parietal fraction, metabolite and metabolic bioproduct.

In any one of the embodiments of the second set of embodiments in the food product and related compositions, methods and systems, the food product and related compositions, methods and systems are for use in increasing the blood bioavailability of at least one amino acid derived from said proteins of plant origin.

According to a third set of embodiments, a non-therapeutic use is described of a composition and related food products, methods and systems, for increasing the blood bioavailability of at least one amino acid derived from a protein of plant origin in a subject taking—through oral route—said protein of plant origin or said at least one amino acid or a peptide of plant origin comprising said at least one amino acid, In any one of the embodiments of the second set of embodiments, said composition comprises a mixture M comprising, or alternatively, consisting of at least one bacterial strain, or a derivative thereof, selected from the group comprising, or alternatively, consisting of:
a bacterial strain belonging to the species Lactobacillus paracasei identified as Lactobacillus paracasei DG® and deposited at the National Collection of Cultures of Microorganisms of the Pasteur Institute in Paris under the accession number CNCM I-1572,
a bacterial strain belonging to the species Lactobacillus paracasei identified as Lactobacillus paracasei LPC-S01™ and deposited at Sammlung von Mikroorganismen und Zellkulturen GmbH (DSMZ) under accession number DSM 26760,
a bacterial strain belonging to the species Bifidobacterium breve identified as Bifidobacterium breve BbIBS01 and deposited at Deutsche Sammlung von Mikroorganismen und Zellkulturen GmbH (DSMZ) under deposit number DSM 33231,
a bacterial strain belonging to the species Bifidobacterium breve identified as Bifidobacterium breve BbIBS02 and deposited at Deutsche Sammlung von Mikroorganismen und Zellkulturen GmbH (DSMZ) under deposit number DSM 33232,
a bacterial strain belonging to the species Bifidobacterium animalis identified as Bifidobacterium animalis subsp. lactis BlIBS01 and deposited at Deutsche Sammlung von Mikroorganismen und Zellkulturen GmbH (DSMZ) under deposit number DSM 33233,
a bacterial strain belonging to the species Lactobacillus plantarum identified as Lactobacillus plantarum LpIBS01 and deposited at Deutsche Sammlung von Mikroorganismen und Zellkulturen GmbH (DSMZ) under deposit number DSM 33234, and
a mixture thereof; and, In any one of the embodiments of the third set of embodiments, said composition can comprise comprises at least one acceptable pharmaceutical or food grade additive and/or excipient, wherein said at least one amino acid is selected from the group A comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

According to a fourth set of embodiments, a method is described and related compositions, food products and systems, for increasing the blood bioavailability of at least one amino acid derived from a protein of plant origin in a subject taking—through oral route—said protein of plant origin or said at least one amino acid or a peptide of plant origin comprising said at least one amino acid, In any one of the embodiments of the fourth set of embodiments said method comprises administering a composition comprising a mixture M comprising or, alternatively, consisting of at least one bacterial strain or a derivative thereof, selected from the group comprising or, alternatively, consisting of:
a bacterial strain belonging to the species Lactobacillus paracasei identified as Lactobacillus paracasei DG® and deposited at the National Collection of Cultures of Microorganisms of the Pasteur Institute in Paris under the accession number CNCM I-1572, a bacterial strain belonging to the species *Lactobacillus paracasei* identified as *Lactobacillus paracasei* LPC-S01™ and deposited at Sammlung von Mikroorganismen und Zellkulturen GmbH (DSMZ) under accession number DSM 26760, a bacterial strain belonging to the species *Bifidobacterium breve* identified as *Bifidobacterium breve* BbIBS01 and deposited at Deutsche Sammlung von Mikroorganismen und Zellkulturen GmbH (DSMZ) under deposit number DSM 33231, a bacterial strain belonging to the species *Bifidobacterium breve* identified as *Bifidobacterium breve* BbIBS02 and deposited at Deutsche Sammlung von Mikroorganismen und Zellkulturen GmbH (DSMZ) under deposit number DSM 33232, a bacterial strain belonging to the species *Bifidobacterium animalis* identified as *Bifidobacterium animalis* subsp. *lactis* BlIBS01 and deposited at Deutsche Sammlung von Mikroorganismen und Zellkulturen GmbH (DSMZ) under deposit number DSM 33233, a bacterial strain belonging to the species *Lactobacillus plantarum* identified as *Lactobacillus plantarum* LpIBS01 and deposited at Deutsche Sammlung von Mikroorganismen und Zellkulturen GmbH (DSMZ) under deposit number DSM 33234, and a mixture thereof; and, optionally, said composition comprises at least one acceptable pharmaceutical or food grade additive and/or excipient, and wherein, said at least one amino acid is selected from the group A comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

According to a fifth set of embodiments, a probiotic bacterial strain (I.i) *Lactobacillus paracasei* DG® CNCM I-1572 (freeze-dried in powder form), is described and related compositions, food products, methods and systems, for use in increasing the blood bioavailability of at least one amino acid derived from a protein of plant or animal origin, preferably from a protein of plant origin, in a subject taking—through oral route—said protein or at least one amino acid or a peptide of plant origin comprising said at least one amino acid.

According to a sixth set of embodiments, a probiotic bacterial strain (I.ii) *Lactobacillus paracasei* LPC-S01™ DSM 26760 (freeze-dried in powder form), is described and related compositions, food products, methods and systems, for use in increasing the blood bioavailability of at least one amino acid derived from a protein of plant or animal origin, preferably from a protein of plant origin, in a subject taking—through oral route—said protein or at least one amino acid or a peptide of plant origin comprising said at least one amino acid.

The examples set forth above are provided to give those of ordinary skill in the art a complete disclosure and description of how to make and use the embodiments of the bacteria, materials, compositions food products, methods and systems of the disclosure, and are not intended to limit the scope of what the inventors regard as their disclosure. Those skilled in the art will recognize how to adapt the features of the exemplified compositions and related methods and systems to additional compositions methods and systems according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

The invention claimed is:

1. A method for increasing blood bioavailability of at least one amino acid from a protein of plant origin in a subject, the method comprising
administering to a vegetarian or vegan subject taking through oral route,
said protein of plant origin,
said at least one amino acid, and/or
a peptide of plant origin comprising said at least one amino acid,
a composition comprising a mixture comprising
at least one bacterial strain, or a derivative thereof, the at least one bacterial strain selected from:
a bacterial strain belonging to the species *Lactobacillus paracasei* identified as *Lactobacillus paracasei* DG and deposited at the National Collection of Cultures of Microorganisms of the Pasteur Institute in Paris under the accession number CNCM I-1572, and
a bacterial strain belonging to the species *Lactobacillus paracasei* identified as *Lactobacillus paracasei* LPC-S01 and deposited at Sammlung von Mikroorganismen und Zellkulturen GmbH (DSMZ) under accession number DSM 26760, or
a mixture thereof, and the derivative thereof selected from at least one tyndallized bacterial strain, at least one sonicated bacterial strain, at least one inactivated bacterial strain, at least one lysate of bacterial strain, at least one paraprobiotic of bacterial strain, at least one postbiotics of bacterial strain or a mixture thereof,
alone or in combination with
a bacterial strain belonging to the species *Bifidobacterium breve* identified as *Bifidobacterium breve* BbIBS01 and deposited at Deutsche Sammlung von Mikroorganismen und Zellkulturen GmbH (DSMZ) under deposit number DSM 33231,
a bacterial strain belonging to the species *Bifidobacterium breve* identified as *Bifidobacterium breve* BbIBS02 and deposited at Deutsche Sammlung von Mikroorganismen und Zellkulturen GmbH (DSMZ) under deposit number DSM 33232,
a bacterial strain belonging to the species *Bifidobacterium animalis* identified as *Bifidobacterium animalis* subsp. *lactis* BIIBS01 and deposited at Deutsche Sammlung von Mikroorganismen und Zellkulturen GmbH (DSMZ) under deposit number DSM 33233,
a bacterial strain belonging to the species *Lactobacillus plantarum* identified as *Lactobacillus plantarum* LpIBS01 and deposited at Deutsche Sammlung von Mikroorganismen und Zellkulturen GmbH (DSMZ) under deposit number DSM 33234, and
a mixture thereof,
the administering performed to increase blood bioavailability of the at least one amino acid derived from a protein of plant origin in the vegetarian or vegan subject.

2. The method according to claim 1, wherein said composition comprises at least one acceptable pharmaceutical or food grade additive and/or excipient and wherein said at least one amino acid is selected from the group comprising arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

3. The method according to claim 1, wherein said at least one amino acid is selected from the group comprising asparagine, alanine, methionine, aspartic acid, histidine, valine, tryptophan, leucine, phenylalanine, isoleucine, tyrosine and mixtures thereof.

4. The method according to claim 1, wherein said mixture comprises at least one bacterial strain, or a derivative thereof, selected from:
*Lactobacillus paracasei* DG CNCM I-1572,
*Lactobacillus paracasei* LPC-S01 DSM 26760,
and a mixture thereof.

5. The method of claim 4, wherein the mixture comprises a mixture of
*Lactobacillus paracasei* DG CNCM I-1572, and *Lactobacillus paracasei* LPC-S01 DSM 26760,
at a 1:1 by weight ratio.

6. The method according to claim 4, wherein said mixture further comprises at least one bacterial strain, or a derivative thereof, selected from:
*Bifidobacterium breve* BbIBS01 DSM 33231,
*Bifidobacterium breve* BbIBS02 DSM 33232,
*Bifidobacterium animalis* subsp. *lactis* BIIBS01 DSM 33233,
*Lactobacillus plantarum* LpIBS01 DSM 33234, and
a mixture thereof.

7. The method according to claim 1, further comprising administering to the subject at least one protein of plant origin, and/or at least one peptide of plant origin, and/or at least one amino acid.

8. The method according to claim 7, wherein said at least one amino acid is selected from comprising arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

9. The method according to claim 1, wherein said vegan or vegetarian subject suffers from a disease, symptom and/or disorder related with a protein deficiency or with an increased protein requirement.

10. The method according to claim 9, wherein said disease, symptom and/or disorder related with said protein deficiency or with said increased protein requirement is selected from: decrease in metabolic efficiency, decrease in corpusculated elements in the blood, changes in healing processes, decrease in muscle strength, decrease in muscle mass, muscle depletion, weight loss, decrease in athletic performance, early fatigue, difficulty in concentrating, anxiety, changes in sleep, changes in mood, increased susceptibility to infections, digestive deficiency, changes in blood sugar, increased cholesterol, changes in blood-chemical parameters, malnutrition syndrome, osteoporosis, decrease in at least one protein-based component of an organism selected from nails, hair, skin, enzymes, neurotransmitters, hormones and immunoglobulins.

11. A method for increasing in a subject the blood bioavailability of at least one amino acid from said proteins of plant origin, the method comprising
administering to the subject a food product comprising proteins of plant origin, and
a mixture comprising at least one bacterial strain selected from:

*Lactobacillus paracasei* DG deposited at the National Collection of Cultures of Microorganisms of the Pasteur Institute in Paris under the accession number CNCM I-1572,

*Lactobacillus paracasei* LPC-S01 and deposited at Sammlung von Mikroorganismen und Zellkulturen GmbH (DSMZ) under accession number DSM 26760,

*Bifidobacterium breve* BbIBS01 and deposited at Sammlung von Mikroorganismen und Zellkulturen GmbH (DSMZ) under accession number DSM 33231,

*Bifidobacterium breve* BbIBS02 and deposited at Sammlung von Mikroorganismen und Zellkulturen GmbH (DSMZ) under accession number DSM 33232,

*Bifidobacterium animalis* subsp. *lactis* BIIBS01 and deposited at Sammlung von Mikroorganismen und Zellkulturen GmbH (DSMZ) under accession number DSM 33233,

*Lactobacillus plantarum* LpIBS01 and deposited at Sammlung von Mikroorganismen und Zellkulturen GmbH (DSMZ) under accession number DSM 33234, and a mixture thereof.

12. A method for increasing the blood bioavailability of at least one amino acid from a protein of plant origin in a subject, the method comprising administering to the subject a composition comprising a mixture comprising at least one bacterial strain or a derivative thereof selected from:

a bacterial strain belonging to the species *Lactobacillus paracasei* identified as *Lactobacillus paracasei* DG and deposited at the National Collection of Cultures of Microorganisms of the Pasteur Institute in Paris under the accession number CNCM I-1572, a bacterial strain belonging to the species *Lactobacillus paracasei* identified as *Lactobacillus paracasei* LPC-S01 and deposited at Sammlung von Mikroorganismen und Zellkulturen GmbH (DSMZ) under accession number DSM 26760, a bacterial strain belonging to the species *Bifidobacterium breve* identified as *Bifidobacterium breve* BbIBS01 and deposited at Deutsche Sammlung von Mikroorganismen und Zellkulturen GmbH (DSMZ) under deposit number DSM 33231, a bacterial strain belonging to the species *Bifidobacterium breve* identified as *Bifidobacterium breve* BbIBS02 and deposited at Deutsche Sammlung von Mikroorganismen und Zellkulturen GmbH (DSMZ) under deposit number DSM 33232, a bacterial strain belonging to the species *Bifidobacterium animalis* identified as *Bifidobacterium animalis* subsp. *lactis* BIIBS01 and deposited at Deutsche Sammlung von Mikroorganismen und Zellkulturen GmbH (DSMZ) under deposit number DSM 33233, a bacterial strain belonging to the species *Lactobacillus plantarum* identified as *Lactobacillus plantarum* LpIBS01 and deposited at Deutsche Sammlung von Mikroorganismen und Zellkulturen GmbH (DSMZ) under deposit number DSM 33234, and a mixture thereof;

the mixture in combination with said protein of plant origin, said at least one amino acid or a peptide of plant origin comprising said at least one amino acid.

13. The method according to claim 12 wherein, said composition comprises at least one acceptable pharmaceutical or food grade additive and/or excipient, and wherein, said at least one amino acid is selected from the group comprising or, alternatively, consisting of: arginine, glutamine, citrulline, serine, asparagine, glycine, threonine, alanine, ornithine, methionine, proline, lysine, aspartic acid, histidine, valine, glutamic acid, tryptophan, leucine, phenylalanine, isoleucine, cysteine, tyrosine and mixtures thereof.

* * * * *